US008062652B2

(12) United States Patent
Kuzma

(10) Patent No.: US 8,062,652 B2
(45) Date of Patent: Nov. 22, 2011

(54) COMPOSITIONS AND METHODS FOR TREATING PRECOCIOUS PUBERTY

(75) Inventor: Petr Kuzma, Princeton, NJ (US)

(73) Assignee: Endo Pharmaceuticals Solutions Inc., Chadds Ford, PA (US)

(*) Notice: Subject to any disclaimer, the term of this patent is extended or adjusted under 35 U.S.C. 154(b) by 364 days.

(21) Appl. No.: 11/155,822

(22) Filed: Jun. 17, 2005

(65) Prior Publication Data

US 2006/0019903 A1 Jan. 26, 2006

Related U.S. Application Data

(60) Provisional application No. 60/580,520, filed on Jun. 17, 2004.

(51) Int. Cl.
*A61F 2/00* (2006.01)
*A61K 38/00* (2006.01)
*A61K 38/09* (2006.01)
*A61K 31/765* (2006.01)
*A61P 5/02* (2006.01)
*A01N 31/14* (2006.01)

(52) U.S. Cl. ..... 424/423; 514/1.1; 514/10.3; 514/722.4; 514/899

(58) Field of Classification Search .................. None
See application file for complete search history.

(56) References Cited

U.S. PATENT DOCUMENTS

| | | |
|---|---|---|
| 2,513,014 A | 6/1950 | Fields |
| 3,921,632 A | 11/1975 | Bardani |
| 4,285,987 A | 8/1981 | Ayer |
| 4,298,002 A | 11/1981 | Ronel et al. |
| 4,846,793 A | 7/1989 | Leonard et al. |
| 4,871,094 A | 10/1989 | Gall et al. |
| 4,959,217 A | 9/1990 | Sanders |
| 4,994,028 A | 2/1991 | Leonard et al. |
| 5,004,614 A | 4/1991 | Staniforth |
| 5,035,891 A | 7/1991 | Runkel et al. |
| 5,266,325 A | 11/1993 | Kuzma |
| 5,273,752 A | 12/1993 | Ayer |
| 5,292,515 A | 3/1994 | Moro |
| 5,614,223 A | 3/1997 | Sipos |
| 5,756,127 A | 5/1998 | Grisoni |
| 5,817,343 A | 10/1998 | Burke |
| 5,854,382 A | 12/1998 | Loomis |
| 5,876,761 A | 3/1999 | Bodmer et al. |
| 5,894,458 A * | 4/1999 | Takizawa et al. .......... 369/13.17 |
| 6,159,490 A | 12/2000 | Deghenghi |
| 6,337,318 B1 * | 1/2002 | Trigg et al. ..................... 514/15 |
| 6,361,797 B1 | 3/2002 | Kuzma et al. |
| 2004/0071736 A1 | 4/2004 | Quinn et al. |
| 2004/0097419 A1 | 5/2004 | Petersen et al. |
| 2005/0143303 A1 | 6/2005 | Quay et al. |

FOREIGN PATENT DOCUMENTS

| | | |
|---|---|---|
| EP | 0246653 | 11/1987 |
| EP | 314206 B1 | 5/1989 |
| EP | 0 384 646 A1 | 6/1993 |
| FR | 821383 A | 12/1937 |
| GB | 1 306 541 A | 2/1973 |
| WO | WO 98/44964 A1 | 10/1998 |
| WO | WO-02/49573 A2 | 6/2002 |
| WO | WO 02/078597 * | 10/2002 |
| WO | WO-2004/071736 A2 | 8/2004 |
| WO | WO 2005/013936 A2 | 2/2005 |
| WO | WO-2005/041873 A2 | 5/2005 |
| WO | WO-2006/099288 A2 | 9/2006 |
| WO | WO-2008/061355 A1 | 5/2008 |

OTHER PUBLICATIONS

Schlegel et al., Effective Long-Term Androgen Suppression in Men with Prostate Cancer using A Hydrogel Implant with the GnRH Agonist Histrelin, 2001, Urology 58(4):578-582.*
Langer, "Implantable Controlled Release Systems," Pharmac. Ther. (1983), vol. 21 pp. 35-51.*
Gennaro A.R., Remington: the Science and Practice of Pharmacy, 19th Edition, p. 1662.*
Lan NaLee, "Volume of Blood in a Human" from http://hypertextbook.com/facts/1998/LanNaLee.shtml, (1998) updated (2001.*
Shi et al. (Expert Opin. Drug Deliv. 2005, 2(6), pp. 1039-1058).*
Precocious Puberty [online] May 2010 retrieved from: http://www.childrensmemorial.org/depts/endocrinology/precocious-puberty.aspx; 4 pages.*
Ostrenski (Gynecology 2001, Lippinocott Williams & Wilkins, p. 12) 2 pages.*
Mayoclinic precocious puberty [online] retrieved from http://www.mayoclinic.com/health/precociouspuberty/DS00883 on Jul. 14, 2011; 9 pages.*
Burradell, L. B. et al., "Histrelin: A Review of its Pharmacological Properties and Therapeutic Role in Central Precocious Puberty," *Drugs*, vol. 45, No. 4, Apr. 1993, pp. 570-588; published by Adis International Limited.
Feuillan, P. P. et al., "Follow-up of children and young adults after GnRH-agonist therapy for central precocious puberty," *J. Endocrinol. Invest.*, vol. 24, 2001, pp. 734-736; published by Editrice Kurtis.
Berge, et al.,; "*Pharmaceutical Salts*" J. Pharm. Sci., 1977 66:1-19.
Higuchi, et al.; "*Pro-Drugs as Novel Delivery Systems*" vol. 14 of the ACS Symposium Series, 1975.
Roche, et al.,; "*Bioreversible Carriers in Drug Design*" American Pharm. Association and Pergamon Press, 1987.
Schlegel et al., Effective Long-Term Androgen Suppression in Men with Prostate Cancer using A Hydrogel Implant with the GnRH Agonist Histrelin, 2001, Urology 58(4):578-582.

(Continued)

*Primary Examiner* — Ernst Arnold
(74) *Attorney, Agent, or Firm* — Gilberto M. Villacorta; Jeffrey R. Lomprey; Foley & Lardner LLP

(57) ABSTRACT

The present invention is directed to the controlled delivery of gonadotropin-releasing hormone (GnRH) agonists, preferably from a polymeric material that is implanted in the body. More specifically, the present invention relates to compositions comprised of a GnRH agonist, preferably histrelin, in a polymeric material that results in a desired and controlled delivery of a therapeutically effective amount of GnRH agonist over an extended period of time in order to treat central precocious puberty (CPP).

18 Claims, 8 Drawing Sheets

OTHER PUBLICATIONS

Chertin et al., An implant Releasins the Gonadotropin Hormone-Releasing Hormone Agonist Histrelin Maintains Medical Castration for up to 30 Months in Metastatic Prostate Cancer, 2000, J. Urology 163(3):838-844.

American Peptide Company, Inc., Peptide Catalog 2006-2007, pp. 119, 171, 175, 211, 217, 219, 227, 296, 315, 317 and 329.

Bodmer D., et al: "Factors influencing the release of peptides and proteins from biodegradable parenteral depot systems" Journal of Controlled Release, Elsevier, Amsterdam, NL LNKD- DOI:10.1016/0168-3659(92)90014-I, vol. 21, No. 1-3, Jul. 1, 1992, pp. 129-137, XP025702099 ISSN: 0168-3659 [retrieved on Jul. 1, 1992].

European Search Report for EP/00904513, completed Mar. 27, 2003.

European Search Report for EP/92300394, completed Sep. 28, 1992.

European Search Report for EP/92300395, dispatched Feb. 27, 2995.

International Search Report PCT/US2009/048475 dated Jun. 1, 2010.

Non-final Office Action for U.S. Appl. No. 11/372,749, mail date Feb. 5, 2008.

Non-final Office Action for U.S. Appl. No. 12/490,971, mail date Sep. 14, 2010.

Non-final Office Action received for U.S. Appl. No. 12/490,971 dated Feb. 2, 2011.

Notice of Allowance for U.S. Appl. No. 12/240,690, mail date Mar., 26, 2010.

Notice of Allowance for U.S. Appl. No. 12/171,999, mail date Mar. 22, 2010.

Notice of Allowance received for U.S. Appl. No. 12/490,979 dated Feb. 4, 2011.

International Preliminary Report on Patentability received for PCT/US2009/048475 dated Jan. 5, 2011.

O'Donnell, et al "Therapeutic Potential of a Long Acting Somatostatin Analogue in Gastrointestinal Diseases" GUT, 1989, vol. 30, pp. 1165-1172.

Office Action for U.S. Appl. No. 07/589,957, mail date Oct. 17, 1991.

Prommer, "Established and Potential Therapeutic Applications of Octreotide in Palliative Care", Support Care Cancer, 2008, vol. 16, pp. 1117-1123.

Remington's Pharmaceutical Sciences, Osol., A. ed., Mack Publishing Co., (1980), 4 pages (cover and table of contents only).

Spitz, et al. "GnRH Superanalog Implants for Prostate Cancer" Proceedings of the 12th International Congress of Endocrinology, 2004, pp. 389-395.

Supplementary European Search Report for EP/06738004, completed Jun. 23, 2010.

* cited by examiner

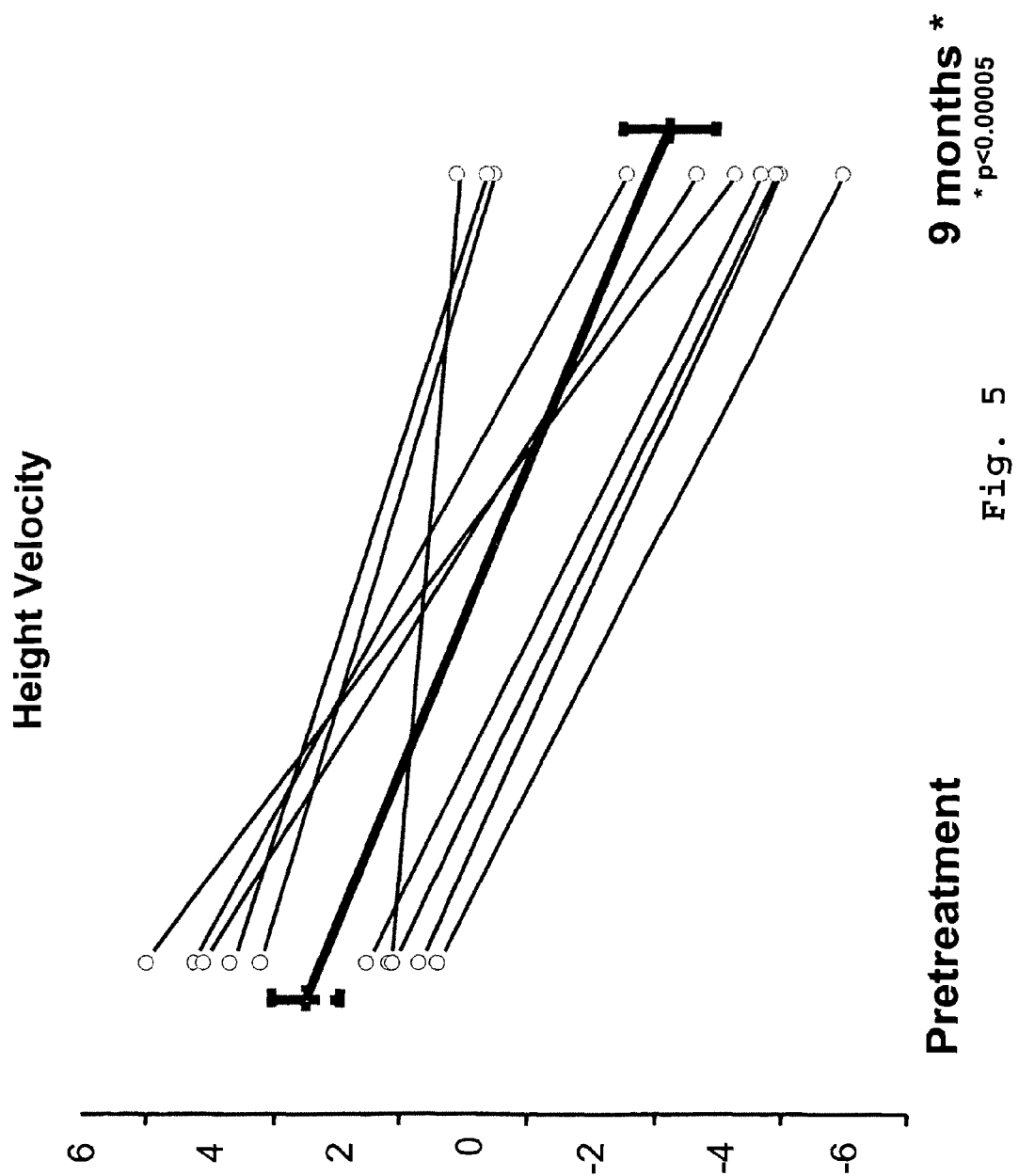

COMPOSITIONS AND METHODS FOR TREATING PRECOCIOUS PUBERTY

REFERENCE TO RELATED APPLICATIONS

This application claims priority from U.S. Provisional Application Ser. No. 60/580,520 filed Jun. 17, 2004, the contents of which are incorporated by reference in its entirety.

BACKGROUND OF THE INVENTION

The present invention is directed to the controlled delivery of gonadotropin-releasing hormone (GnRH) agonists, preferably from a polymeric material that is implanted in the body. More specifically, the present invention relates to compositions comprised of a GnRH agonist, preferably histrelin, in a polymeric material that results in a desired and controlled delivery of a therapeutically effective amount of GnRH agonist in order to treat central precocious puberty (CPP).

There is a wide range of ages at which individuals normally start puberty. Girls usually develop breasts and then pubic hair between the ages of 8 and 13 years. Menstrual periods typically start at 12 to 13 years of age. Girls will often experience moodiness and become more irritable during puberty. Boys normally develop testicular enlargement and then pubic hair between the ages of 9 and 14 years. Underarm and facial hair, as well as deepening of the voice, typically occur between the ages of 13 and 16 years.

In the United States, an estimated one out of every 10,000 children suffers from central precocious puberty or premature puberty. This condition is evident when girls under the age of eight years and boys under the age of nine years develop signs of sexual maturity, such as the early onset of secondary sexual characteristics, increase in growth rate, advancement of skeletal age beyond chronological age. Signs or symptoms of CPP include, but are not limited to, the development of secondary sex characteristics such as breasts, testicle growth, or pubic hair.

True precocious puberty is the result of premature initiation of the function of the hypothalamic-pituitary axis. Premature release of the luteinizing hormone releasing hormone (LHRH) by the hypothalamus triggers secretion of the pituitary gonadotropin hormones. As a consequence, the gonads function at an inappropriately early age. Precocious puberty per se has many subdivisions: isosexual, heterosexual, gonadotropin-dependent (true precocious puberty), gonadotropin-independent, male-limited (familial testotoxicosis), cerebral, central, and idiopathic (unknown) precocious puberty. Precocious puberty is also known as familial testotoxicosis, gonadotropin-independent familial sexual precocity, and pubertas praecox.

In the majority of cases of precocious puberty, the cause is unknown. In some instances, the pituitary signals the ovaries and testicles to make female and male hormones at an earlier than usual time. In other cases, signs of puberty occur prematurely because of abnormalities in the ovaries, testicles, or adrenal glands. Tests are usually necessary to determine whether the cause of precocious puberty is in the brain or in another area of the body. Usually precocious puberty is idiopathic (unknown cause). In some instances, it is due to an endocrine disorder. Cerebral precocious puberty is associated with a brain abnormality, for example a tumor of the central nervous system, including hypothalamic hamartomas, infections, head trauma, hydrocephalus, or hypothyroidism. Precocious puberty may also be a feature of McCune-Albright syndrome, neurofibromatosis, Russell-Silver syndrome and disorders of the adrenal glands. Affected individuals may encounter psychological problems due to their accelerated growth and may feel alienated from their peers. They may exhibit increased aggressiveness and hyperactivity. Male-limited precocious puberty (familial testotoxicosis) is considered hereditary.

In females, the breasts start to develop before age 8, or menstruation occurs before age 10, and growth is rapid. In males, onset is before age 10; boys grow facial, underarm, and pubic hair; growth, including that of the penis, accelerates; the voice deepens; and behavior becomes more aggressive. Puberty may take place before age 3 in some children. Children with precocious puberty are taller than their peers. Since bone maturity is usually hastened in precocious puberty, closure of growth occurs prematurely, and patients are short in stature in adulthood. In isosexual precocious puberty, feminizing signs appear in girls, masculinization in boys. Heterosexual precocious puberty causes signs of masculine characteristics in girls and feminization in boys. Cerebral precocious puberty differs in cause but mimics true precocious puberty. Central precocious puberty is attended by changes that concern the central nervous system. Gonadotropin-dependent precocious puberty is marked by high gonadotropin levels in girls. Gonadotropin-independent precocious puberty usually affects boys, who have low levels of gonadotropin. Idiopathic precocious puberty is associated with EEG (Electroencephalogram) irregularities in girls. The cause of the unusual brain waves is unclear.

Treatments that affect the hypothalamic-pituitary-gonadal axis can effectively reduce hormones to pre-pubertal levels. This may arrest and prevent further development of secondary sex characteristics. Reduction of gonadotropins will allow for normal physical and psychological growth and development. Natural maturation occurs when gonadotropins return to pubertal levels following discontinuation of treatment.

GnRH (also referred to as luteinizing hormone-releasing hormone (LH-RH)) acts on the anterior pituitary gland to effect release of hormones that affect activity of the reproductive organs. GnRH is produced by the hypothalamic region of the brain and controls the reproductive cycle by acting on the anterior pituitary gland to affect release of luteinizing hormone (LH) and follicular stimulating hormone (FSH), which in turn act on the gonads to stimulate the synthesis of steroid hormones and to stimulate gamete maturation. The natural GnRH peptide is a hydrophilic decapeptide. Agonist analogs of GnRH may be used to control fertility, for example, low doses of GnRH agonists may stimulate ovulation and larger doses may block ovulation in females and suppress spermatogenesis in males through classic negative feedback principles.

Conventional treatment of CPP includes administration of GnRH agonists. Synthetic analogues of GnRH agonists are considered to be more effective than the natural agonists. Examples of GnRH agonists include, but not limited to, leuprolide (Lupron Depot®), goserelin (Zoladex®) and histrelin (Supprelin®), buserelin (Suprefact®), nafarelin (Synarel®) and triptorelin (De-capeptyl®, Trelstar Depot®). Many of these formulations involve monthly intramuscular injections of the drug. While usually effective in suppressing gonadotropin secretion, the monthly injections are painful, expensive, and inconvenient (monthly visits to the clinic nurse or physician). In some patients, gonadotropin suppression is not sustained by a monthly schedule of injections and the GnRH analog needs to be administered at 3-week or even 2-week intervals (1-3). For children, the daily dose of histrelin for treatment of CPP is typically about 10 µg/kg/day, which is equivalent to about 300 to about 600 µg histrelin per day.

Histrelin is a synthetic nonapeptide agonist of the naturally occurring GnRH. Initially the drug stimulates release of GnRH; however, chronic use desensitizes responsiveness of the pituitary gonadotropin, causing a reduction in ovarian and testicular steroidogenesis.

In view of the foregoing, a method for treating central precocious puberty and therapeutic compositions of GnRH agonists are provided.

SUMMARY OF THE INVENTION

The subject of the present invention is a drug delivery device useful in a method for controlled delivery of GnRH agonists, preferably histrelin, to a patient over an extended period of time. This device is useful in the treatment of CPP.

Thus, in one embodiment, the present invention provides an implantable drug delivery device containing histrelin. In one particular embodiment, the device is a hydrogel polymer material.

In a further embodiment, the present invention provides a method of delivery of a therapeutically effective amount of GnRH agonists to a patient. This method involves implanting the patient with a drug delivery device as described herein.

In another embodiment, the present invention provides for a method of obtaining immediate release of GnRH agonist upon implantation in a patient. Desirably, the GnRH agonist, such as histrelin, is released following implantation to achieve therapeutically effective amounts of histrelin in vivo to treat CPP.

In a further embodiment, the present invention provides for a method of preventing loss of GnRH agonist from an implant during storage.

Other aspects and advantages of the invention will be readily apparent form the detailed description of the invention.

BRIEF DESCRIPTION OF THE DRAWINGS

For a fuller understanding of the nature and advantages of the present invention, reference should be had to the following detailed description taken in connection with the accompanying drawings.

DETAILED DESCRIPTION OF THE INVENTION

Figure 1:
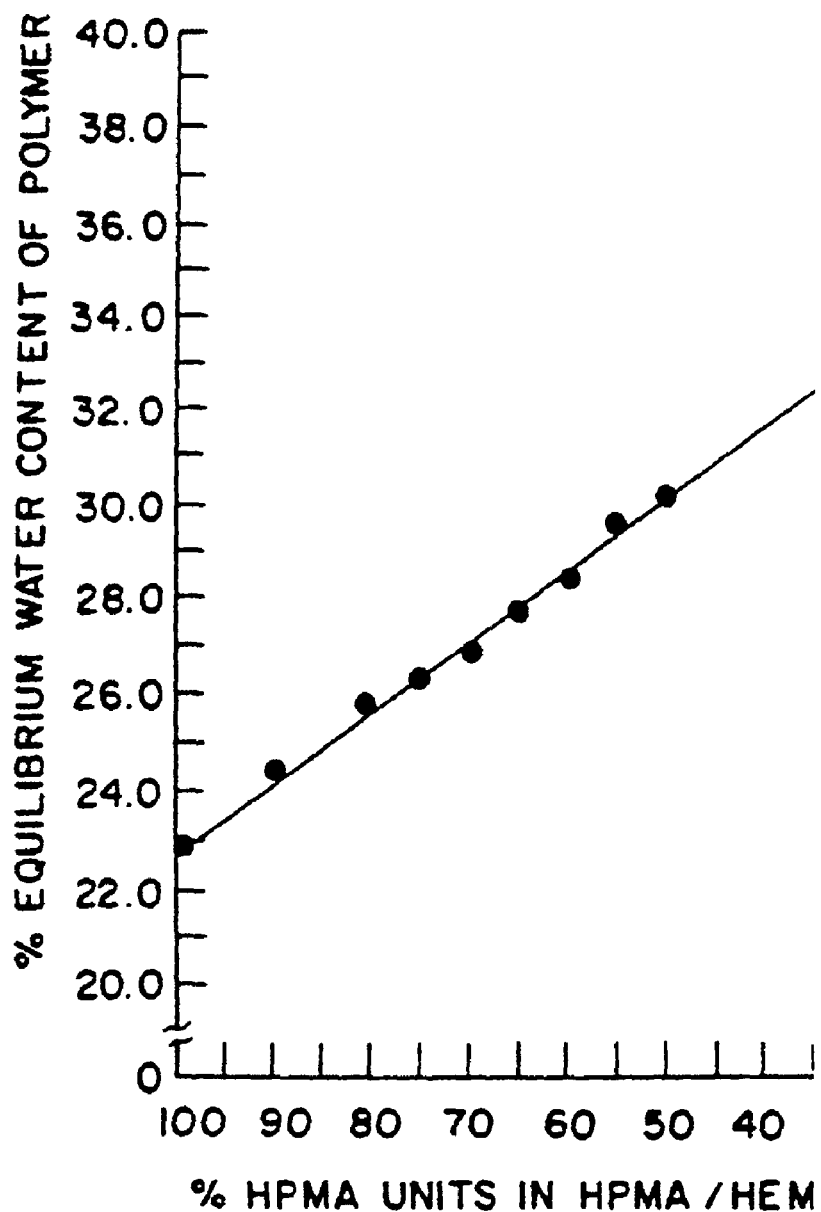
FIG. 1 is a graph showing the linear relationship between the equilibrium water content vs. the weight percent content of hydroxypropyl methacrylate (HPMA) units in crosslinked HEMA/HPMA polymers at their maximum state of hydration.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. For example about 50% means in the range of 45%-55%.

"Controlled release" or "controlled release formulation" refers to a formulation designed to consistently release a predetermined, therapeutically effective amount of drug or other active agent such as a polypeptide or a synthetic compound below toxic levels over an extended period of time, with the result being a reduction in the number of treatments necessary to achieve the desired therapeutic effect. Preferably the amount of the drug or active agent in the implantable formulations according to embodiments of the present invention establish a therapeutically effective plasma concentration of the drug over a period of 1 month or longer. In the matter of the present invention, a controlled formulation would decrease the number of treatments necessary to achieve the desired effect in terms of decreased estradiol levels or testosterone levels, or an improvement in symptoms associated with central precocious puberty. The controlled release formulations of the present invention achieve a desired pharmacokinetic profile in a subject, preferably commencement of the release of the active agent substantially immediately after placement in a delivery environment, followed by consistent, sustained, preferably zero-order or near zero-order release of the active agent.

The terms "patient" and "subject" mean all animals including humans. Examples of patients or subjects include humans, cows, dogs, cats, goats, sheep, and pigs.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "prodrug" refers to compounds that are rapidly transformed in vivo to yield the parent compounds of the above formula, for example, by hydrolysis in blood. A thorough discussion is provided in T. Higuchi and V. Stella, "Prodrugs as Novel Delivery Systems," Vol. 14 of the A.C.S.

Symposium Series, and in Bioreversible Carriers in Drug Design, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetraethylammonium, methylamine, dimethlyamine, trimethlyamine, triethlyamine, ethylamine, and the like. (See, for example, S. M. Barge et al., "Pharmaceutical Salts," J. Pharm. Sci., 1977, 66:1-19 which is incorporated herein by reference.).

"Treatment" refers to the administration of medicine or the performance of medical procedures with respect to a patient, for either prophylaxis (prevention) or to cure the infirmity or malady in the instance where the patient is afflicted.

A "therapeutically effective amount" is an amount sufficient to decrease, prevent, or ameliorate the symptoms associated with a medical condition. In the context of hormonal therapy it can also mean to normalize body functions or hormone levels in disease or disorders. For example, a therapeutically effective amount of a controlled release formulation of histrelin is a predetermined amount calculated to achieve the desired effect, e.g., to effectively decrease estradiol levels or testosterone levels in a patient or decrease the symptoms of central precocious puberty.

In various embodiments, the novel drug delivery device of the invention is designed for implantation into the body of the animal to which the histrelin formulation is to be delivered. The drug delivery devices of the invention are desirably implants containing histrelin in a reservoir, optionally together with another active agent and/or a pharmaceutically acceptable carrier. Such reservoir devices may be composed of hydrophobic or hydrophilic polymers, co-monomers, metals, or other suitable materials. Alternatively, the drug delivery devices may be hydrogels, or other polymeric or co-monomer materials, made up of a matrix having histrelin and any other optional active agents or carriers interspersed throughout. Preferably, the histrelin is dispersed homogeneously throughout the matrix. Yet other suitable implants are known to those of skill in the art and may be readily selected.

The novel implant drug delivery devices of the invention, in a preferred aspect, are highly useful in the controlled, sustained release of histrelin to animals, e.g., humans, sheep, dogs, cats, turkeys, cattle, etc.

The amount of histrelin and any other agents employed in the drug delivery devices of the invention will depend not only on the desired daily dose but also on the number of days that dose level is to be maintained. While this amount can be calculated empirically, the actual dose delivered is also a function of any interaction with materials and the carrier, if employed in the device.

Thus, the drug delivery device may contain a pharmaceutically acceptable carrier which may be in the form of suspending media, solvents, aqueous systems, and solid substrates or matrices. These carriers are known to those of skill in the art and are not intended to be a limitation on the present invention.

One aspect of the invention is a controlled release pharmaceutical composition comprising histrelin acetate in a controlled release hydrogel device. The composition of the present invention is capable of providing, upon administration to a patient, a release profile of histrelin extending over at least 2 months, preferably at least about 6 months or more. In some embodiments, the histrelin may be released over a period of about 18 months to about 2 years. Preferably histrelin is contained within the hydrogel and the formulation releases a therapeutically effective amount of histrelin over an extended period of time. A therapeutically effective amount is an amount of histrelin, preferably histrelin acetate, that when administered to a patient or subject, ameliorates a symptom of central precocious puberty. In a preferred embodiment, the formulation may further include pharmaceutically acceptable excipients.

When the compositions of the present invention are administered to a patient, the concentration of histrelin in the patient's plasma over time (release profile) may extend over a period of at least 2 months, preferably about 6 months or more. In a further embodiment, the histrelin may be released over a period of about 18 months to about 2 years. The compositions may provide a mean plasma concentration of histrelin of about 0.2 ng/ml to about 2 ng/ml. The compositions may provide a mean plasma concentration at steady state of histrelin in a human patient of from about 0.4 ng/ml to about 0.6 ng/ml. Steady state is the point at which the amount of drug administered over a dosing interval equals the amount of drug being eliminated over that same period.

The hydrogel is a homogeneous homopolymer or copolymer having a predetermined equilibrium water content (EWC) value formed by the polymerization of a mixture of ethylenically unsaturated monomer A and ethylenically unsaturated monomer B, for example, 2-hydroxyethyl methacrylate (HEMA) and hydroxypropyl methacrylate (HPMA). The predetermined EWC may be calculated by determining the EWC values of the hydrogel homopolymer of hydrophilic monomer A (homopolymer A) and the hydrogel homopolymer of hydrophilic monomer B (homopolymer B); determining the relationship of the EWC values of the homogeneous copolymers AB versus the chemical composition of said copolymers AB; selecting the targeted EWC value and determining the chemical composition of copolymer AB having the targeted EWC value; forming a polymerizable mixture of monomer A and monomer B in amounts sufficient to yield copolymer AB having the targeted EWC value; and effect the polymerization reaction to yield copolymer AB characterized by the targeted EWC value.

Liquid polymerizable material useful in the hydrophilic products include a wide variety of polymerizable hydrophilic, ethylenically unsaturated compounds, in particular, hydrophilic monomers such as the monoester of an acrylic acid or methacrylic acid with a polyhydroxy compound having an esterifiable hydroxyl group and at least one additional hydroxyl group such as the monoalkylene and polyalkylene polyols of methacrylic acid and acrylic acid, e.g., 2-hydroxyethyl methacrylate and acrylate, diethylene glycol methacrylate and acrylate, propylene glycol methacrylate and acrylate, dipropylene glycol methacrylate and acrylate, glycidyl methacrylate and acrylate, glyceryl methacrylate and acrylate, and the like; the 2-alkenamides, e.g., acrylamide, methacrylamide, and the like; the N-alkyl and N,N-dialkyl substituted acrylamides and methacrylamides such as N-methylmethacrylamide, N,N-dimethylmethacrylamide, and the like; N-vinylpyrrolidone; the alkyl-substituted N-vinylpyrrolidones, e.g., methyl substituted N-vinylpyrrolidone; N-vinylcaprolactam; the alkyl-substituted N-vinylcaprolactam, e.g., N-vinyl-2-methylcaprolactam, N-vinyl-3,5-dimethylcaprolactam, and the like. Acrylic and methacrylic acid can also be useful in these formulations.

Mixtures of hydrophilic monomers are employed in the polymerization reaction. The type and proportion of monomers are selected to yield a homogeneous polymer, preferably a crosslinked homogeneous polymer, which on hydration possesses the desired EWC value for the contemplated application or use. As shown in FIG. 1, this value can be predetermined by preparing a series of copolymers using different monomer ratios, e.g., mixtures of HEMA and HPMA of varying ratios, ascertaining the EWC values of the copolymers, and plotting the relationship of % HPMA (or % HEMA) units in the HPMA/HEMA copolymers vs. weight percent EWC of the copolymers.

In some instances the polymerization of certain hydrophilic monomeric mixtures may result in homogeneous hydrophilic copolymers which dissolve, to a varying extent, in an aqueous medium. In such cases, a small amount, e.g., up to 3 percent, of a copolymerizable polyethylenically unsaturated crosslinking agent can be included in the monomeric mixture to obtain homogeneous crosslinked copolymers which are water-insoluble as well as water-swellable. Slightly crosslinked homopolymer of HEMA has a EWC value of about 38%. Crosslinked copolymers of HEMA and HPMA have EWC values below 38%. On the other hand, crosslinked copolymers of HEMA and acrylamide exhibit EWC values above 38 w/v %, e.g., upwards to approximately 75 weight %, and higher. Therefore, depending on the useful or effective elution rate of the active compound, e.g., drug, that is required of a hydrogel delivery system for a particular application, one skilled in the art, by following the teachings disclosed herein, can tailor-make copolymer hydrogel membranes which will elute the drug at the required rate. Preferred copolymers contain about 15 to 70 weight % of HEMA units and from about 85 to 30 weight % of units of a second ethylenic monomer and possess predetermined EWC values in the range of from about 20 to about 75 %, preferably 25%. Highly preferred homogenous copolymers are those made from hydrophilic monomeric mixtures containing from about 80 weight % HPMA, and from about 20 weight % HEMA. In further embodiments, the mixture may further contain a small amount of a polyethylenically unsaturated crosslinking agent, e.g., trimethylolpropane trimethacrylate ("TMPTMA").

Various aspects of the invention include homogeneous hydrophilic copolymers whose homogeneous polymer structure is formed via the polymerization of a mixture of hydrophilic monomers described previously; and the drug delivery device which utilize the homogeneous polymer cartridges in the delivery system. The polymerization of a mixture of hydrophilic monomers and hydrophobic monomers yields heterogeneous polymers. When hydrophobic segments are present in the polymer, the interfacial free energy increases thus enhancing protein adsorption and mineralization after implantation in an animal. Hydrogels of polyHEMA were measured to have interfacial free energy close to zero. According to the interfacial free energy interpretation, hydrogels of strictly hydrophilic components would strongly appear to be biocompatible with body tissue. Slightly crosslinked polyHEMA is a homogeneous, hydrophilic "homopolymer" (disregarding the relatively small quantities of polymerized crosslinking agent therein) of relatively fixed characteristics or values. Techniques of altering the "homopolymer" polyHEMA to impart to it additional characteristics or properties are difficult, time-consuming, and oftentimes result in erratic property behavior. On the other hand, mixtures of HEMA with varying quantities of other polymerizable hydrophilic comonomer(s) can be polymerized to give predictable homogeneous hydrophilic copolymers having (predetermined) tailor-made properties.

Useful crosslinking agents which can be included in the polymerizable reaction medium include, for example, the polyethylenically unsaturated compounds having at least two polymerizable ethylenic sites, such as the di-, tri- and tetraethylenically unsaturated compounds, in particular, the tri-unsaturated crosslinking agents with/without the di-unsaturated crosslinking compounds, for example, divinylbenzene, ethylene glycol dimethacrylate and diacrylate, propylene glycol dimethacrylate and diacrylate; and the di-, tri- and tetraacrylate or methacrylate esters of the following polyols: triethanolamine, glycerol, pentaerythritol, 1,1,1-trimethylolpropane; and others.

The polymerization reaction can be carried out in bulk or with an inert solvent. Suitable solvents include water; organic solvents such as water-soluble lower aliphatic monohydric alcohols as well as polyhydric alcohols, e.g., glycol, glycerine, dioxane, etc.; and mixtures thereof.

Compounds useful in the catalysis of the polymerizable ethylenically unsaturated compounds include the free-radical compounds and/or initiators of the type commonly used in vinyl polymerization such as the organic peroxides, percarbonates, hydrogen peroxides, and alkali metal sulfates. Illustrative examples include cumene hydroperoxide, t-butyl hydroperoxide, benzoyl peroxide, bis(4-t-butylcyclohexyl) peroxydicarbonate, hydrogen peroxide, 2,4-dichlorobenzoyl peroxide, acetyl peroxide, di-n-propyl peroxydicarbonate, di-t-butyl peroxide, di-sec-butyl peroxydicarbonate, ammonium sulfate, potassium sulfate, and sodium sulfate. A preferred catalyst is one which is effective at moderately low temperature such as at about 20°-80° C., such as tert-butyl peroctoate, benzoyl peroxide, and di(secbutyl) peroxydicarbonate. A conventional redox polymerization catalyst can also be employed. Preferably, polymerization of the ethylenic compounds can be effected using radiation, e.g., U.V., X-Ray, gamma radiation, microwave, or other well-know forms of radiation. A preferred catalyst for U.V. cure is benzoin methyl ether. Catalysts and/or initiators and/or radiation are employed in a catalytically effective amount to optimize the polymerization reaction.

In a preferred embodiment, small cylindrically shaped implants containing within their core histrelin, preferably histrelin acetate, and optionally, a pharmaceutically acceptable carrier. The membrane thickness (between the interior and exterior surfaces) of the implant is substantially uniform, and serves as a rate-limiting barrier for the release of the contained agent. Such implants can be plasticized or hydrated and reshaped into other geometrically shaped articles for use in various medical applications. The hydrophilic implant as a xerogel, readily absorbs water. In a hydrated state it is referred to as a hydrogel. In, either form, it is biocompatible and non-toxic to the host and non-biodegradable. It is, of course, water-swellable and water-insoluble. When the hydrogel attains its maximum level of hydration, the water content of the hydrogel is referred to as "equilibrium water content".

The percent water content of the hydrogel (any state of hydration) is determined as follows:

$$\frac{\text{weight of hydrogel} - \text{weight of dry polymer(xerogel)}}{\text{weight of hydrogel}} \times 100$$

In the manufacture of the implantable formulation, several factors are considered. The release profile (delay time, release rate, and duration) is determined; the hydrophilic polymeric material is identified; and the diffusivity of the active agent through it (as a rate-limiting membrane) is measured. The hydration profile of the rate-limiting membrane for a given active agent may be readily determined by preparing a film of the selected polymer and subjecting it to a diffusion study, using a two compartment vertical glass cell, as is well known in the art.

The diffusion coefficient and the water content at which diffusion begins (i.e., below which substantially no diffusion occurs—hereinafter "% $H_d$") are determined. A series of membranes is prepared from various polymers. The membranes are then hydrated to their capacity and their equilibrium water contents are measured. The fully hydrated membranes are placed in the two-compartment, vertical glass cells to measure and plot the diffusion of the macromolecular composition through the membrane materials at the various equilibrium water contents. The equilibrium water content of the most hydrated membrane through which no diffusion is detected (i.e., none of the active agent diffuses into the receptor cell) is the % $H_d$ for the system being tested. This can be accomplished by plotting a curve of the permeability vs. equilibrium water content.

The permeability results (diffusion coefficients) are obtained according to Fick's First Law of Diffusion, by use of the equation:

$$\frac{dQ}{dt} = \frac{APC_d}{1}$$

wherein dQ/dt is the flux through the membrane material (μg/hr); it is measured as the slope of the linear part of the curve of cumulative transport versus time; wherein A is the area of the membrane (cm$^2$); wherein P is the membrane's permeability coefficient (cm$^2$/hr), or $DK_d$, wherein D is the diffusivity of the membrane (cm$^2$/hr), and $K_d$ is the partition coefficient for the membrane/donor solution; wherein 1 is the membrane thickness as measured at the end of the experiment (cm); and wherein $C_d$ is the concentration of the donor solution (μg/cm$^3$).

The release delay profile is then determined. Another series of polymeric membranes can be prepared, again varying the amounts of crosslinker and monomers. These membranes are then hydrated, but only partially, i.e., to a water content less than or equal to % $H_d$. The partially hydrated membranes are placed in two-compartment vertical glass cells to measure and plot the diffusion of the active compound through the membranes versus time. Buffer solutions for the donor and receptor cells may be selected to contact the partially hydrated membranes and further hydrate them at approximately the same rate at which they will hydrate in the delivery environment. The time between commencement of the diffusion study, i.e., addition of the active agent to the donor cell, and the detection of a pharmaceutically effective concentration of the active agent in the receptor cell is the release delay time for that combination of polymer and initial percent hydration.

In order to determine the physical dimensions of the cylindrically-shaped device, the total amount of active agent to be delivered must be determined. This is the product of the desired daily dosage and the duration of delivery. In preferred embodiments, the duration of delivery is at least about 2 months, more preferably about 6 months or longer and the desired daily dosage is, for example, about 60 μg to about 70 μg of histrelin.

The volume of the cylindrical reservoir (core) of a cylindrically-shaped device is equal to $\Pi r_i^2$ h wherein $r_i$ is the radius of the reservoir and h is its height. The formula for steady state release from a cylinder is:

$$[dQ/dt] = [2\Pi h DK_d C_d]/[\ln(r_o/r_i)]$$

wherein $r_o$ is the outside radius of the cylindrical device; and wherein $C_d$ is the concentration of drug in the donor solution, i.e., the carrier. Steady state release is obtained when $C_d$ is maintained at saturation. The thickness of the membrane needed for the desired sustained release is, therefore, $r_o$-$r_i$.

The amount of active agent employed will depend not only on the desired daily dose but also on the number of days that dose level is to be maintained. While this amount can be calculated empirically, the actual dose delivered is also a function of any interaction with materials and the carrier, if employed in the device.

In various embodiments, the novel formulation of the present invention may contain a pharmaceutically acceptable carrier which may include, but is not limited to, suspending media, solvents, aqueous systems, and solid substrates or matrices.

Suspending media and solvents useful as the carrier include, for example, oils such as silicone oil (particularly medical grade), corn oil, castor oil, peanut oil and sesame oil; condensation products of castor oil and ethylene oxide; liquid glyceryl triesters of a lower molecular weight fatty acid; lower alkanols; glycols; polyalkylene glycols.

The aqueous systems include, for example, sterile water, saline, dextrose, dextrose in water or saline, and the like. The presence of electrolytes in the aqueous systems may tend to lower the solubility of the macromolecular drug in them.

The solid substrates or matrices include, for example, starch, gelatin, sugars (e.g., glucose), natural gums (e.g., acacia, sodium alginate, carboxymethyl cellulose), and the like.

The carrier may also contain adjuvants such as preserving, stabilizing, wetting and emulsifying agents, and the like.

The hydrating liquid useful in the practice of the invention is typically a liquid simulating the environment in which the active compound will be released, e.g., body fluid, sterile water, tear fluid, physiological saline solution, phosphate buffer solution, and the like. While liquids other than water are useful as the hydrating liquid, the degree to which a hydrophilic membrane is hydrated is referred to as its "water content".

By the expressions "copolymer AB" or "copolymer AB consists essentially of monomer A units and monomer B units" is meant that the addition copolymerization of monomer A and monomer B has been effected through the polymerizable ethylenic bond of the said monomers. By way of illustration, if monomer A is 2-hydroxyethyl methacrylate and monomer B is N-methylacrylamide, copolymer AB contains recurring monomer A units and recurring monomer B units.

Unless the context indicates otherwise, the term "copolymer" includes polymers made by polymerizing a mixture of at least two ethylenically unsaturated monomers.

By the term "HEMA unit(s)" is meant the structure

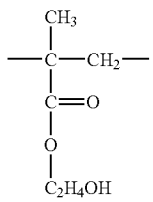

recurring in the polymer obtained by polymerizing hydrophilic material containing 2-hydroxyethyl methacrylate ("HEMA").

By the term "HPMA unit(s)" is meant the structure

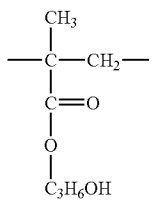

obtained by polymerizing hydrophilic material containing hydroxypropyl methacrylate ("HPMA").

In one embodiment, a pharmaceutical formulation of the present invention comprises a formulation of histrelin within a mixture of HEMA and HPMA copolymer, preferably about 45% HEMA and 55% HPMA. In preferred embodiments, the pharmaceutical formulation comprises about 25 to about 150 milligrams of histrelin, preferably about 35-45 milligrams of histrelin base. The formulation may further comprise between about 0.5% to about 20% excipients. In a preferred embodiment, the formulation further comprises about 2% stearic acid.

In one suitable embodiment, hydrogels are suited as implantable delivery vehicles for use in delivery of histrelin according to the present invention. One hydrogel is prepared by mixing about 60 weight percent to about 95 weight percent comonomers, at least one of which is hydrophilic, and sufficient amounts of a crosslinker and a liquid diffusion enhancer which is miscible with the comonomers, to yield a homogenous copolymer hydrogel having the equilibrium water content (EWC) value in the range from about 20% to about 85%. More preferably, homogenous copolymer hydrogel has a EWC value in the range from about 25% to about 35%. More preferably, another hydrogel is prepared by mixing about 40 weight percent to about 95 weight percent comonomers, at least one of which is hydrophilic, and sufficient amounts of a crosslinker and optionally a liquid diffusion enhancer which is miscible with the comonomers, to yield a homogenous copolymer hydrogel having the equilibrium water content (EWC) value in the range from about 20% to about 85%, more preferably from about 25% to about 35%.

The polymerizable liquid mixture may also contain about 1 weight percent to about 50 weight percent diffusion enhancer which may be readily selected from among C1-C4 alkyl alcohol, allyl alcohol, tetrahydrofliryl alcohol, cyclohexyl alcohol, diethylene glycol, polyethylene glycols, glycerol, acetone, ethylene glycol monomethyl ether, ethylene glycol monoethyl ether, glyceryl isopropylidene ether dioxane, tetrahydrofuran; ethyl acetate; dimethyl sulfoxide; water, and mixtures thereof. The crosslinker and comonomers may be readily selected by one of skill in the art. Hydrogels and methods of preparation are generally described in International Patent Application Number PCT/US00/01664, filed Jan. 26, 2000 for "Hydrogel Compositions Useful for the Sustained Release of Macromolecules and Methods of Making Same." Other suitable hydrogels may be readily selected by one of skill in the art. See, e.g., U.S. Pat. Nos. 5,266,325; 4,959,217; and 5,292,515.

Another particularly desirable hydrogel is prepared by mixing about 40 weight percent to about 95 weight percent comonomers, at least one of which is hydrophilic, and sufficient amounts of a crosslinker and optionally a liquid diffusion enhancer which is miscible with the comonomers, to yield a homogenous copolymer hydrogel having the equilibrium water content (EWC) value in the range from about 20% to about 85%. More preferably, homogenous copolymer hydrogel has a EWC value in the range from about 25% to about 35%.

In one embodiment, the hydrogel comprises 2-hydroxyethyl methacrylate (HEMA) and hydroxypropyl methacrylate (HPMA). The hydrogel may also further comprise a crosslinking agent, such as, for example (TMPTMA). In a preferred embodiment, the hydrogel comprises about 45% of HEMA, about 54.5% HPMA and about 0.5% TMPTMA.

In a further embodiment, a delivery device capable of providing a sustained release of a therapeutically effective amount of GnRH agonist is provided. Preferably the controlled release is achieved of a period of time of at least 6 months or more, more preferably about 1 to about 2 years. In a preferred embodiment, the delivery device comprises a hydrogel, wherein the composition of the hydrogel is based upon the desired daily dose and release profile. In a preferred embodiment, a delivery device capable of providing controlled release of about 60 µg to about 70 µg of histrelin per day is provided. In a more preferred embodiment, the delivery device provides about 65 µg of histrelin per day.

While not bound by theory, the diffusion of the drug occurs through water channels in the hydrogel. Controlling the water content of the hydrogel allows for manipulation of the release profile of the agent within the hydrogel. The release may also be manipulated by the geometry of the drug delivery device, including, for example, the area, wall thickness and diameter. Treatment of particular diseases or conditions may require higher or lower therapeutic levels or differing release profiles, which may be achieved through the design of the drug delivery device of the present invention.

The hydrating liquid useful in the hydrogels used in the invention is typically a liquid simulating the environment in which the active compound will be released, e.g., body fluid, sterile water, tear fluid, physiological saline solution, phosphate buffer solution, and the like. While liquids other than water are useful as the hydrating liquid, the degree to which a hydrophilic membrane is hydrated is referred to as its "water content."

In another suitable embodiment, the implant may be in the form of an osmotic pump, such as described by Alza (see, e.g., U.S. Pat. Nos. 4,285,987 and 5,273,752) or Merck (see, e.g., European Patent No. 314,206), among others. In another example, the implant device may be composed of a hydrophobic membrane material, such as ethylmethacrylate (EMA) and ethylenevinylacetate (EVA). Other suitable implant delivery devices include bioresorbable polymer systems (see, e.g., International Patent Application No. W098/44964, Bioxid and Cellomeda; U.S. Pat. Nos. 5,756,127 and 5,854,382). Suitable bioresorbable implant devices have been described in the literature and may be composed of, for example, polyesters, polyanhydrides, or lactic acid/glycolic acid copolymers (see, e.g., U.S. Pat. No. 5,817,343 Alkermes Inc.).

Regardless of whether the delivery device is composed of a hydrogel, EVA/EMA polymer, bioresorbable material, metal or other material, the devices useful in the invention(s) provide sustained release of histrelin over extended periods of time. This time period may range from a month to a year or several years, depending on the desired administration regimen. Preferably, histrelin will be released in daily doses over a period of about 2 months or longer, and preferably over a period of about six months to one year or longer. In some embodiments, the histrelin may be released over a period of about 18 months to about 2 years. It is to be understood that this time factor is a variable depending on the rate-releasing membrane of choice, its interconnecting pore structure, the solubility of the active compound(s) in the liquid medium, and other considerations well known to those skilled in the art.

Where the delivery device is composed of a hydrogel, it may be prepared such that the hydrogel forms the walls of a cavity which contain the active agent. A predetermined amount of histrelin per se or an admixture with an inert, non-toxic material or as a suspension in a non-toxic material or as a suspension in a non-toxic medium, e.g., medical grade silicone oil, is introduced into the cavity to partially fill the core. The void in the core is thereafter sealed to prevent leakage into or out of the vesicle. Preferably this can be accomplished by introducing sufficient polymerizable material into the void to cover the layer of inert material or to substantially or completely fill the void and thereafter effecting a polymerization reaction to form a plug of water-swellable, water-insoluble polymer which seals the opening of the vesicle. The hydrophilic polymer plug, upon maximum hydration, will have an equilibrium water content value of the hydrophilic vesicle. Using polymerizable material comprising ethylenically unsaturated monomer(s) and desirably crosslinking agent(s), a polymer plug grafted to the inner surface of the vesicle can be obtained.

In a currently desired embodiment, hydrophilic cartridges are prepared by the rotational casting of polymerizable material in a tubular mold, as described in U.S. Pat. Nos. 5,266,325 and 5,292,515, which are incorporated herein by reference.

Briefly, the internal radius of the tube is approximately 1.2 to 1.3 mm, and may be larger. The tube is rotated about its longitudinal axis which is maintained parallel to the ground. Rotational speeds are of the order of 2150 rpm, though greater or lesser speeds could be used, e. g., 1000 rpm or less to 3000 rpm and more. The tubes are fabricated of polyethylene, polypropylene, glass, or other suitable materials. When the polymerizable mixture within the spinning tube stabilizes to the predetermined shape, U.V. light at a distance of less than one foot is then directed at the spinning tube for several minutes, e.g., about 7 minutes, to polymerize the mixture to the shaped product. The shaped product is cured and annealed as follows: Thermal Cure: 60 minutes at 65° C.; Postcure: 30 minutes at 95° C.; Annealing: 30 minutes at 115° C. with gradual cooling to about 25° C.

After shaping and polishing the closed end of the cartridge to an oval-like cylindrical profile, there is obtained small cylindrically-shaped objects having smooth, unscored cylindrical surfaces. The cartridge may be of any desired combination of dimensions. For example, the internal radius may be about 0.98 mm; the external radius may be about 1.3 mm; and the length may be about 25 mm, or of larger or smaller dimensions, as desired.

Smooth, unscored cylindrically-shaped objects of various lengths, e.g., up to 25 cm and longer, can also be prepared in accordance with the teachings herein.

Such objects, in a hydrated state or plasticized with a non-toxic, biocompatible material, can be formed into desired shapes. A ring shape, for use as pessaries, surgical implants, etc. Yet other drug delivery devices and implant shapes may be prepared using techniques known to those of skill in the art or purchased from commercial sources.

In preferred embodiments, upon hydration the length of the implantable delivery device is about 32-37 mm, the outside diameter is about 3-3.5 mm, the cartridge walls are about 0.5 mm and the cavity diameter is about 2-2.5 mm.

In a further embodiment, the invention provides for a method of delivering histrelin, alone or in combination with other active agents, upon implantation in a patient. The hydrogel delivery device of the present invention is hydrated with a hydrating liquid prior to implantation in the patient, so as to provide release of histrelin upon implantation.

In another embodiment, a method of inhibiting release of histrelin prior to implantation is provided. The hydrogel implant delivery device of the present invention is stored in a hydrating liquid prior to implantation in the patient, so as to limit release of histrelin from the implant prior to implantation. In preferred embodiments, the hydrating liquid is sodium chloride solution.

The invention provides a method of delivering histrelin, alone or in combination with other active agents, to a veterinary or human patient in need thereof. Typically, such a patient has a disease or condition such as central precocious puberty.

In order to treat a patient, one or more delivery devices as described herein can be implanted subcutaneously in an animal by perforation. Such devices are characterized by a length of 10 to 50 mm, or less (e.g., 6 to 9 mm), an external diameter of 2 to 5 mm, or less (e.g., 1.5 to 1.9 mm). The dimensions of the device (e.g., a cartridge) can vary outside of the limits stated above depending, in particular, on the medical application involved. Animals such as sheep, cows, goats, cattle, and large animals, in general, can tolerate implantation by perforation of larger dimensional drug delivery devices. Implantation can be effected by other means, e.g., open surgery.

In one embodiment, the drug delivery device is a biodegradable matrix, which is bioresorbed and eliminated from the body following completion of the course of therapy, e.g., at least about 2 months, or more preferably about 12 months or longer. Alternatively, a selected delivery device may be removed by surgical means.

A method of treating a disease associated with a hormonal disorder is also provided. The method may include administering histrelin and maintaining a plasma concentration of histrelin of about 0.2 ng/ml to about 2 ng/ml and maintaining a plasma concentration of histrelin at steady state between about 0.4 ng/ml and about 0.6 ng/ml over an extended period of time, preferably at least about 2 months, and more preferably about 6 months or longer. Such hormonal disorders include CPP or the like. In one embodiment, the method may comprise administering one or more delivery devices comprising a hydrogel of about 45% of HEMA, about 54.5% HPMA, about 0.5% TMPTMA and histrelin acetate.

One embodiment is a method of decreasing estradiol levels or testosterone levels by administering histrelin and maintaining a steady state plasma concentration of histrelin between about 0.4 ng/ml and about 0.6 ng/ml, over an extended period of time, preferably at least about 2 months, and more preferably about 6 months or longer. Another embodiment is a method of decreasing symptoms of CPP by administering histrelin and maintaining a plasma concentration of histrelin between about 0.2 ng/ml to about 2 ng/ml over an extended period of time, preferably at least about 2 months, and more preferably about 6 months or longer.

Another embodiment is a method of treating CPP comprising administering at least one hydrogel implant of the present invention, or two or more hydrogel implants of the present invention. In the method, each hydrogel of the two hydrogel implants administered may contain between about 25 to about 150 milligrams of histrelin acetate, preferably about 40 to about 90 milligrams of histrelin acetate, more preferably about 50 milligrams of histrelin acetate and release a therapeutically effective amount of histrelin over a period of at least two months, preferably six months or longer.

In a further embodiment, a method of treating CPP comprises administering one or more implants comprising a hydrogel and histrelin. Preferably, the hydrogel implants contain about 50 milligrams of histrelin acetate and release from about 60 µg to about 70 µg of histrelin acetate substantially upon implantation for a period of at least 2 months, more preferable for about 1 year.

Another aspect is a therapeutic composition of a hydrogel and histrelin, wherein, upon implantation, histrelin is released at a rate that provides and/or maintains a $C_{ss}$ of about 0.2 ng/ml to about 2 ng/ml. A further embodiment is a therapeutic composition of a hydrogel and histrelin, wherein, upon implantation, the histrelin is released at an average rate of from about 60 to about 70 µg/day, preferably an average of about 65 µg daily over an extended period of time, preferably at least about two months, more preferably about six months or longer.

Another embodiment is a controlled release formulation comprising histrelin and a hydrophilic polymer, which permits release of the histrelin at a rate of about 60 µg to about 70 µg per day over about six months or longer in vitro. In a further embodiment, the hydrophilic polymer of the formulation permits release of histrelin at an average rate of about 65 µg per day in vitro.

In a further embodiment, a controlled release formulation comprising histrelin and a hydrophilic polymer is provided that releases from about 140 µg to about 40 µg per day over about six months or longer, more preferably about 135 µg to about 60 µg per day over about six months or longer.

The amount of a pharmaceutically acceptable histrelin, salt, solvated, or prodrug thereof included in the pharmaceutical composition of the present invention will vary, depending upon a variety of factors, including, for example, the specific histrelin used, the desired dosage level, the type and amount of hydrogel used, and the presence, types and amounts of additional materials included in the composition. The amount of histrelin, or a derivative thereof, in the formulation varies depending on the desired dose for efficient drug delivery, the molecular weight, and the activity of the compound. The actual amount of the used drug can depend on the patient's age, weight, sex, medical condition, disease or any other medical criteria. The actual drug amount is determined according to intended medical use by techniques known in the art. The pharmaceutical dosage formulated according to the invention may be administered about once every six months as determined by the attending physician.

Typically, the histrelin is formulated in the implant or other pharmaceutical composition in amounts of about 25 milligrams to about 150 milligrams, preferably about 40 to about 90 milligrams of histrelin. Preferably, the amount of histrelin in the composition is formulated to release from about 60 µg to about 70 µg of histrelin daily and maintain therapeutic levels in the patient's blood at about 0.2 ng/ml to about 2 ng/ml over an extended period of time.

The hydrogel device in which histrelin is contained provides a controlled release of histrelin into the plasma of the patient. Hydrogels suitable for controlling the release rate of histrelin for use in the pharmaceutical compositions of the present invention include polymers of hydrophilic monomers, including, but not limited to HPMA, HEMA and the like. Such hydrogels are also capable of preventing degradation and loss of histrelin from the composition.

In one embodiment, a pharmaceutical formulation of the present invention comprises histrelin acetate contained within a hydrophilic copolymer of 2-hydroxyethyl methacrylate and hydroxypropyl methacrylate. In a preferred embodiment, the copolymer of the pharmaceutical formulation comprises about 45% HEMA and about 55% HPMA. In another preferred embodiment, the formulation further comprises stearic acid.

The amount of the hydrogel included in the pharmaceutical composition of the present invention will vary depending upon a variety of factors, including, for example, the specific matrix used, its molecular weight, its hydrophilicity, the type and amount of histrelin used, and the presence, types and amounts of additional materials included in the composition.

The size, shape and surface area of the implant may also be modified to increase or decrease the release rate of histrelin from the implant.

The formulations of the present invention exhibit a specific, desired release profile which maximizes the therapeutic effect while minimizing adverse side effects. The desired release profile may be described in terms of the maximum plasma concentration of the drug or active agent ($C_{max}$) and the plasma concentration of the drug or active agent at steady state ($C_{ss}$).

Suitably, treatment of CPP or related conditions using the drug delivery devices of the invention may be readily combined with other therapies administered by routes other than through the use of an implantable devices. For example, treatment with histrelin according to the invention may be combined with other treatments or therapies.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLE 1

Hydrogel implants were prepared in accordance with the present invention. In particular, about 45% HEMA, 54.5% HPMA and about 0.5% TMPTMA were admixed with 0.3% benzoinmethylether (BME) and 0.1% percadox-16.

EXAMPLE 2

Figure 2:
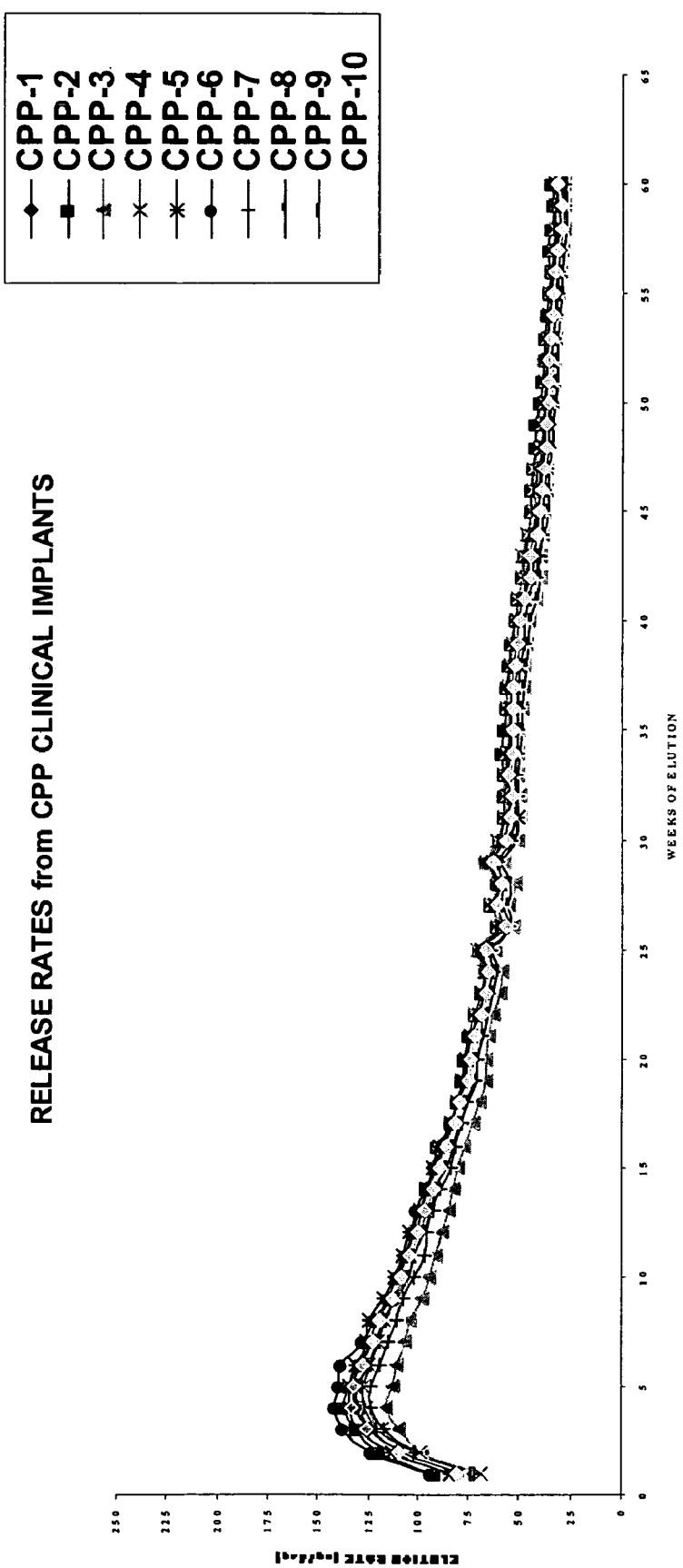
FIG. 2 is a graph of the release profiles of various histrelin implants of the present invention.

Ten histrelin implants were prepared in accordance with the present invention. In particular, the histrelin implants comprised about 45% HEMA and about 55% HPMA. The resulting hydrogel implants exhibited an equilibrium water content (EWC) of about 29%. The implants were prehydrated. The release rates were measured over sixty weeks. The release profile for the histrelin implants is provided in FIG. 2.

EXAMPLE 3

This was an open-label study in which children with CPP were assigned to receive one or two histrelin hydrogel implants, containing 50 mg of histrelin each, depending on their body weight and the ease of insertion of the implant, as determined on a case-by-case basis by the principal investigator and the surgeon performing the insertion. The histrelin implants were supplied in about 2.0 mL of 1.8% sodium chloride solution. Following the first 9 months of the study, the children were assigned to one of two tracks. Children in the first track had their implant(s) removed, and one new implant inserted. The implant remained in place in those in the second track. The children in both tracks continued in the study for an additional 9 months. In total, eleven girls ages 3 to 11 years old were enrolled in this study. Ten of the 11 patients completed at least 12 months of treatment.

Study visits occurred at baseline, 4 weeks (Month 1), 3 months, and then every 3 months for the remainder of the study. Blood samples for determination of histrelin serum concentrations and determination of hormone levels were collected at each clinic visit. GnRH challenge tests were performed with Relefact® LHRH 0.1 mg (=100 µg gonadorelin) intravenous injection before the implant insertion, at month 9, and at month 18 for all patients. GnRH challenge tests were also performed at every visit after month 9 for the patients whose implant(s) remained in place after that time. If at any visit there was incomplete hormonal suppression or if the clinical evaluation indicated disease progression, the implant was to be removed and the child offered a new implant.

All 11 patients were being treated with the GnRH analogs when they entered the study. The duration of treatment at study entry ranged from less than 2 weeks to 39 months. Eight of the patients had been treated for 7 months or less, one for 18 months, one for 21 months, and one for 39 months. The standard treatments were decapeptyl embonate (9 patients), diphereline (1 patient), or both decapeptyl and diphereline (1 patient). These were administered as intramuscular depot injections every 21 to 28 days. The histrelin implant was inserted anywhere from 2 days to 1.5 months after the last depot injection.

Five patients were treated with two implants, and a single implant was inserted in the remaining six patients. One of the patients with two implants had one removed at the time of suture removal; in analyses of data by number of implants, she is included in the group with one implant. At month 9, five patients had their implants removed and had a single new implant inserted. The remaining six patients had their original implant(s) left in place for 18 months.

The standard GnRH treatment had suppressed estradiol levels to below 73 pmol/L in 10 of the 11 patients at the time of implant insertion. None of these 10 patients had an estradiol level greater than 73 pmol/L at any evaluation through month 12, i.e., their values remained within the prepubertal range.

Basal luteinizing hormone (LH) and follicle stimulating hormone (FSH) levels were suppressed due to standard GnRH treatment at baseline and remained suppressed following implant insertion. Suppression of peak LH and FSH responses to GnRH testing was maintained for 9 months following implant insertion in all 11 girls, and for 12 months in the six girls who had their original implants left in place and had GnRH challenge testing at 12 months.

The results of the first 12 months of the study, described below, support the safety and efficacy of the histrelin implant in patients with CPP. This data also suggest that one implant is as effective as two implants in the suppression of estradiol, LH and FSH. Treatment with the histrelin implant maintained suppression of estradiol and basal LH and FSH initiated by treatment with standard GnRH analogs.

Estradiol Levels. Table 1 displays the mean values, and mean changes from baseline, in estradiol levels for the ITT population during 9 months of treatment. The mean values changed little over time, suggesting that the suppression achieved with standard treatment for CPP was maintained during treatment with the histrelin implant.

TABLE 1

Mean Values and Mean Changes in Estradiol (pmol/L) Through Month 9 (ITT Population)

| Visit (Month) | All ITT Patients (N = 11) | | |
|---|---|---|---|
| | N | Mean (SD) | Mean Change (SD) |
| Baseline (Visit 1/Day 1) | 11 | 36.07 (23.462) | |
| Visit 2 (Month 1) | 11 | 35.70 (19.348) | −0.37 (26.839) |
| Visit 3 (Month 3) | 11 | 37.64 (18.424) | 1.56 (12.008) |
| Visit 4 (Month 6) | 11 | 32.56 (22.192) | −3.51 (15.429) |
| Visit 5 (Month 9) | 11 | 26.38 (19.684) | −9.69 (25.012) |

Table 2 displays the estradiol results for subsets of the patients categorized by the number of implants they received. The suppression of estradiol levels was maintained regardless of whether the patients received one or two implants. Within the group of patients who received one implant, the results were similar regardless of baseline weight.

TABLE 2

Mean Values and Mean Changes in Estradiol (pmol/L) Through Month 9 by Number of Implants (ITT Population)

| | N | Mean (SD) | Mean Change (SD) |
|---|---|---|---|
| 1 Implant | | | |
| Baseline (Visit 1/Day 1) | 7 | 34.07 (17.68) | |
| Visit 2 (Month 1) | 7 | 36.47 (22.378) | 2.40 (23.574) |
| Visit 3 (Month 3) | 7 | 32.39 (12.510) | −1.69 (11.688) |
| Visit 4 (Month 6) | 7 | 25.33 (11.523) | −8.74 (12.420) |
| Visit 5 (Month 9) | 7 | 22.56 (17.950) | −11.51 (29.223) |
| 2 Implants | | | |
| Baseline (Visit 1/Day 1) | 4 | 39.58 (34.41) | |
| Visit 2 (Month 1) | 4 | 34.35 (15.570) | −5.23 (35.216) |
| Visit 3 (Month 3) | 4 | 46.83 (25.329) | 7.25 (11.818) |
| Visit 4 (Month 6) | 4 | 45.23 (32.252) | 5.65 (17.586) |
| Visit 5 (Month 9) | 4 | 33.08 (23.520) | −6.50 (18.867) |

Table 3 summarizes the estradiol results after 9 months. Suppression of estradiol levels appeared to be maintained in patients who received new implants at 9 months and also in patients whose original implant(s) remained in place at 9 through 12 months.

TABLE 3

Mean Values and Mean Changes in Estradiol (pmol/L) After 9 Months of Treatment by Track (ITT Population)

| | N | Mean (SD) | Mean Change (SD) from Baseline |
|---|---|---|---|
| First Track (New Implant) | | | |
| Visit 5 (Month 9) | 5 | 31.48 (23.691) | −6.68 (24.968) |
| Visit 6 (Month 12) | 4 | 12.70 (5.560) | −12.93 (10.984) |
| Second Track (1 Implant Left in Place) | | | |
| Visit 5 (Month 9) | 5 | 22.90 (18.530) | −12.20 (30.329) |
| Visit 6 (Month 12) | 5 | 23.56 (16.475) | −11.54 (5.038) |
| Second Track (2 Implants Left in Place) | | | |
| Visit 5 (Month 9) | 1 | 18.30 | −12.20 |
| Visit 6 (Month 12) | 1 | 25.80 | −4.70 |

LH and FSH Levels. Basal gonadotropin levels were suppressed at baseline and remained suppressed following implant insertion. The mean values showed little change during the first 9 months of the study, as shown in Table 4.

TABLE 4

Mean Values and Mean Changes in LH and FSH (mIU/mL) Through Month 9 (ITT Population)

| | All ITT Patients (N = 11) | | |
|---|---|---|---|
| | N | Mean (SD) | Mean Change (SD) |
| LH (mIU/mL) | | | |
| Baseline (Visit 1/Day 1) | 11 | 0.47 (0.358) | |
| Visit 2 (Month 1) | 11 | 0.26 (0.163) | −0.21 (0.425) |
| Visit 3 (Month 3) | 11 | 0.25 (0.199) | −0.22 (0.444) |
| Visit 4 (Month 6) | 11 | 0.20 (0.144) | −0.28 (0.416) |
| Visit 5 (Month 9) | 11 | 0.20 (0.121) | −0.28 (0.409) |
| FSH (mIU/mL) | | | |
| Baseline (Visit 1/Day 1) | 11 | 1.20 (0.429) | |
| Visit 2 (Month 1) | 11 | 1.07 (0.531) | −0.13 (0.445) |
| Visit 3 (Month 3) | 11 | 1.11 (0.602) | −0.09 (0.499) |
| Visit 4 (Month 6) | 11 | 1.08 (0.517) | −0.12 (0.438) |
| Visit 5 (Month 9) | 11 | 1.07 (0.535) | −0.13 (0.427) |

Table 5 shows the mean values and mean changes in LH and FSH for patients categorized the by the number of implants. The mean changes in LH were larger for patients with two implants than for those with one implant. The subgroup of patients with one implant showed a mean decrease in FSH during the first month of treatment. This decrease was maintained through month 9. The subgroup of patients with two implants showed a small mean increase in FSH during the first 9 months of treatment.

The pattern of changes in LH was similar regardless of baseline weight in the subgroup of patients with one implant. The patients who weighed >40 kg at baseline had larger mean decreases in FSH at every evaluation (ranging from −0.37 to −0.50 mIU/mL) than did those who weighed ≦40 kg at baseline (ranging from −0.13 to −0.25 mIU/mL).

TABLE 5

Mean Values and Mean Changes in LH and FSH (mIU/mL) Through Month 9 by Number of Implants (ITT Population)

| | N | Mean (SD) | Mean Change (SD) |
|---|---|---|---|
| LH (mIU/mL) | | | |
| 1 Implant | | | |
| Baseline (Visit 1/Day 1) | 7 | 0.39 (0.107) | |
| Visit 2 (Month 1) | 7 | 0.31 (0.177) | −0.07 (0.198) |
| Visit 3 (Month 3) | 7 | 0.31 (0.227) | −0.07 (0.229) |
| Visit 4 (Month 6) | 7 | 0.23 (0.170) | −0.16 (0.199) |
| Visit 5 (Month 9) | 7 | 0.24 (0.127) | −0.14 (0.172) |
| 2 Implants | | | |
| Baseline (Visit 1/Day 1) | 4 | 0.63 (0.597) | |
| Visit 2 (Month 1) | 4 | 0.18 (0.096) | −0.45 (0.635) |
| Visit 3 (Month 3) | 4 | 0.14 (0.068) | −0.48 (0.639) |
| Visit 4 (Month 6) | 4 | 0.14 (0.068) | −0.48 (0.639) |
| Visit 5 (Month 9) | 4 | 0.12 (0.057) | −0.51 (0.620) |
| FSH (mIU/mL) | | | |
| 1 Implant | | | |
| Baseline (Visit 1/Day 1) | 7 | 1.19 (0.426) | |
| Visit 2 (Month 1) | 7 | 0.93 (0.325) | −0.26 (0.346) |
| Visit 3 (Month 3) | 7 | 0.90 (0.289) | −0.29 (0.353) |
| Visit 4 (Month 6) | 7 | 0.87 (0.287) | −0.31 (0.363) |
| Visit 5 (Month 9) | 7 | 0.89 (0.372) | −0.30 (0.420) |
| 2 Implants | | | |
| Baseline (Visit 1/Day 1) | 4 | 1.23 (0.499) | |
| Visit 2 (Month 1) | 4 | 1.33 (0.772) | 0.10 (0.560) |
| Visit 3 (Month 3) | 4 | 1.48 (0.873) | 0.25 (0.580) |
| Visit 4 (Month 6) | 4 | 1.45 (0.666) | 0.23 (0.359) |
| Visit 5 (Month 9) | 4 | 1.40 (0.673) | 0.18 (0.250) |

Table 6 summarizes the LH and FSH results after 9 months of treatment. Suppression of LH and FSH levels was maintained in patients who received new implants at 9 months and also in patients whose original implant(s) remained in place at 9 and 12 months.

TABLE 6

Mean Values and Mean Changes in LH and FSH (mIU/mL) After 9 Months of Treatment by Track (ITT Population)

| | N | Mean (SD) | Mean Change (SD) from Baseline |
|---|---|---|---|
| LH (mIU/mL) | | | |
| First Track (New Implant) | | | |
| Visit 5 (Month 9) | 5 | 0.23 (0.174) | −0.39 (0.602) |
| Visit 6 (Month 12) | 4 | 0.28 (0.171) | −0.13 (0.171) |
| Second Track (1 Implant Left in Place) | | | |
| Visit 5 (Month 9) | 5 | 0.18 (0.045) | −0.20 (0.158) |
| Visit 6 (Month 12) | 5 | 0.22 (0.045) | −0.16 (0.167) |
| Second Track (2 Implants Left in Place) | | | |
| Visit 5 (Month 9) | 1 | 0.10 | −0.10 |
| Visit 6 (Month 12) | 1 | 0.10 | −0.10 |
| FSH (mIU/mL) | | | |
| First Track (New Implant) | | | |
| Visit 5 (Month 9) | 5 | 1.42 (0.502) | 0.02 (0.589) |
| Visit 6 (Month 12) | 4 | 1.25 (0.635) | −0.13 (0.772) |
| Second Track (1 Implant Left in Place) | | | |
| Visit 5 (Month 9) | 5 | 0.86 (0.378) | −0.28 (0.228) |
| Visit 6 (Month 12) | 5 | 1.04 (0.483) | −0.10 (0.447) |

TABLE 6-continued

Mean Values and Mean Changes in LH and FSH (mIU/mL) After 9 Months of Treatment by Track (ITT Population)

|  | N | Mean (SD) | Mean Change (SD) from Baseline |
|---|---|---|---|
| Second Track (2 Implants Left in Place) | | | |
| Visit 5 (Month 9) | 1 | 0.40 | −0.10 |
| Visit 6 (Month 12) | 1 | 0.40 | −0.10 |

Results of GnRH Challenge Test. The results of the GnRH challenge tests are summarized in Table 7 for the ITT population. At baseline, there were mean increases in LH and FSH 20 minutes after administration of LHRH. The mean value for LH decreased at 40 and 60 minutes, whereas the value for FSH remained elevated. During treatment with the histrelin implant, there was no mean increase in LH or FSH in response to administration of LHRH.

TABLE 7

Summary of GnRH Challenge Test Results (ITT Population)

|  |  | Mean | | | |
|---|---|---|---|---|---|
|  | N | 0 Min | 20 Min | 40 Min | 60 Min |
| LH (mIU/mL) | | | | | |
| Baseline (Visit 1/Day 1) | 11 | 0.47 | 1.30 | 1.15 | 0.91 |
| Visit 3 (Month 3) | 5 | 0.22 | 0.22 | 0.28 | 0.22 |
| Visit 4 (Month 6) | 10 | 0.16 | 0.18 | 0.19 | 0.15 |
| Visit 5 (Month 9) | 11 | 0.20 | 0.24 | 0.22 | 0.22 |
| FSH (mIU/mL) | | | | | |
| Baseline (Visit 1/Day 1) | 11 | 1.20 | 1.66 | 1.62 | 1.63 |
| Visit 3 (Month 3) | 5 | 0.92 | 0.94 | 0.96 | 0.92 |
| Visit 4 (Month 6) | 10 | 1.11 | 1.10 | 1.09 | 1.11 |
| Visit 5 (Month 9) | 11 | 1.07 | 1.11 | 1.11 | 1.09 |

The results were similar for the subsets of patients who had one or two implants and for the patients with one implant categorized by baseline weight.

GnRH challenge tests were done at month 12 only for patients whose implants were left in place at month 9 (second track). At month 12, these patients continued to show no mean increase in LH and FSH levels in response to administration of LHRH.

These results suggest that standard GnRH analog treatment had resulted in markedly suppressed gonadotropin response to GnRH stimulation before the patients received the histrelin implants. Complete suppression of peak LH and FSH to GnRH testing was maintained for 9 months following implant insertion in all 11 girls and for 12 months in those whose implants were left in place.

IGF Levels. The mean value for IGF-1 was 350.18 ng/mL at baseline and 311.82 ng/mL at month 9, yielding a mean change of −38.36 ng/mL. The mean value for IGF-BP3 was 5.47 mg/L at baseline and 6.51 mg/L at Month 9, yielding a mean change of 1.04 mg/L.

No patient showed a shift from baseline to Month 9 in IGF-1 levels. Ten (91%) of the patients had values within the normal range at both evaluations, and the remaining one (9%) patient had values above the normal range at both evaluations.

Seven (64%) patients had IGF-BP3 values at baseline that were above the normal range for their age and sex. One of these patients had a value within the normal range at Month 9, whereas the remaining six patients had values that remained above normal. Four (36%) patients had normal IGF-BP3 values at baseline. One of these patients had a value within the normal range at Month 9. The remaining three patients, identified below, had shifts from within the normal range at baseline to above the normal range at month 9.

Patient 104 (3 years old), whose value increased from 2.7 mg/L at baseline to 5.3 mg/L at month 9 (normal range, 0.8 to 3.8 mg/L)

Patient 107 (8 years old), whose values increased from 4.7 mg/L at baseline to 5.9 mg/L at month 9 (normal range, 1.2 to 4.7 mg/L)

Patient 110 (8 years old), whose value increased from 4.2 mg/L at baseline to 5.9 mg/L at month 9 (normal ranges, 1.2 to 4.7 mg/L at baseline and 1.6 to 4.0 mg/L at month 9)

Bone Age by X-Ray. Determination of each patient's bone age by x-ray was performed at screening and again at month 9. At screening, the mean bone age was 10.10 years (range, 4.5 to 12.75 years) whereas the mean chronologic age was 8.4 years (range, 3.58 to 11.00 years). Thus, bone age was advanced compared to the chronological age in all girls at the time of implant insertion. The bone age increased by a mean of 0.35 years, to 10.46 years, at month 9. The increase in chronologic age at month 9 was 0.96 years. Therefore, there was no advancement in bone age during treatment with the histrelin implant and, in fact, the bone age advancement regressed during treatment.

Histrelin levels. FIG. 3A displays the serum histrelin concentrations for each patient with 1 implant (track 1) at all evaluation times and FIG. 3B displays the serum histrelin concentrations for each patient with 2 implants (track 2) at all evaluation times. Histrelin levels remained fairly constant over time for most patients.

Physical Findings. Temperature, blood pressure, heart rate, weight, and height were measured at every evaluation. The mean changes that occurred in temperature, blood pressure, and heart rate were small, showed no time-related trends, and were not clinically meaningful.

It is difficult to interpret the mean values for height and weight for the patients in this population whose age range (3 to 11 years) covers times of different rates of growth in children. Therefore, height, weight, and BMI data for each patient at baseline and month 12 were transformed to Z-scores based on the patients' age in months and sex (data not shown) Most of the patients had values for all Z-scores that were between −1.96 ($5^{th}$ percentile) and 1.96 ($95^{th}$ percentile). The following patients had values that were outside that range:

Height adjusted for age: Patients 105 (2.02 at baseline and 1.58 at month 12); Patient 107 (2.48 at baseline and 2.18 at month 12); and Patient 111 (1.98 at baseline and 2.16 at month 12).

Weight adjusted for age: Patient 103 (1.98 at baseline and 1.98 at month 12); Patient 107 (2.41 at baseline and 2.45 at month 12); and Patient 111 (2.10 at baseline and 2.32 at month 12).

BMI adjusted for age: Patient 102 (−2.49 at baseline to −1.25 at month 12); Patient 103 (2.04 at baseline and 1.95 at month 12); and Patient 107 (1.88 at baseline and 2.04 at month 12).

Thus, most of these patients had Z-scores that were either above the $95^{th}$ percentile or below the $5^{th}$ percentile at both baseline and month 12, or had values above the $95^{th}$ at baseline which decreased to below the $95^{th}$ percentile by month 12. The only patient with an increase from below the $95^{th}$ percentile at baseline to above the $95^{th}$ percentile at month 12 was Patient 107, for BMI only.

Figure 6:
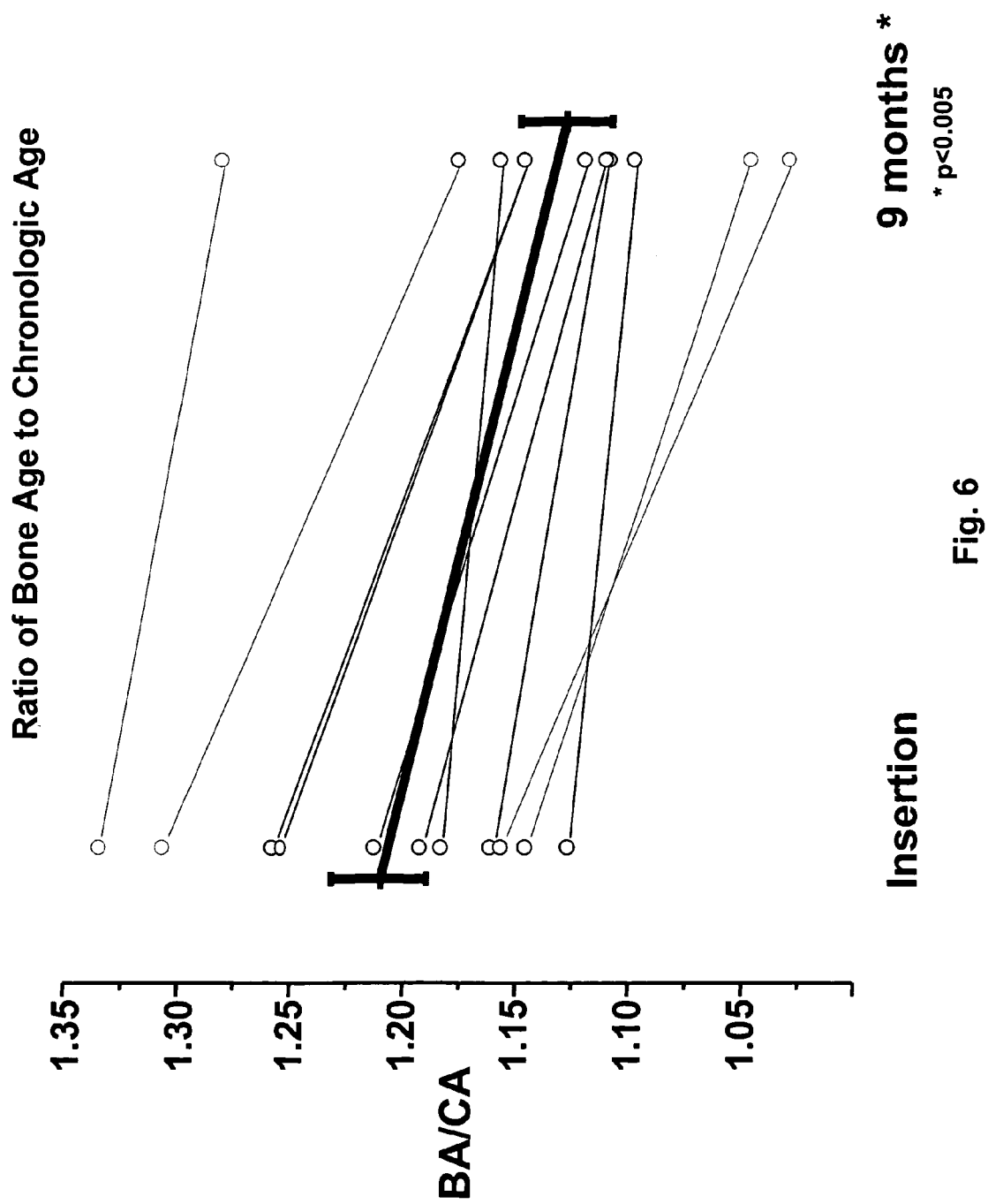
FIG. 6 is a graph of the ratio of bone age:chronologic age at pretreatment and 9 months following insertion of an histrelin implant of the present invention.
Figure 1:
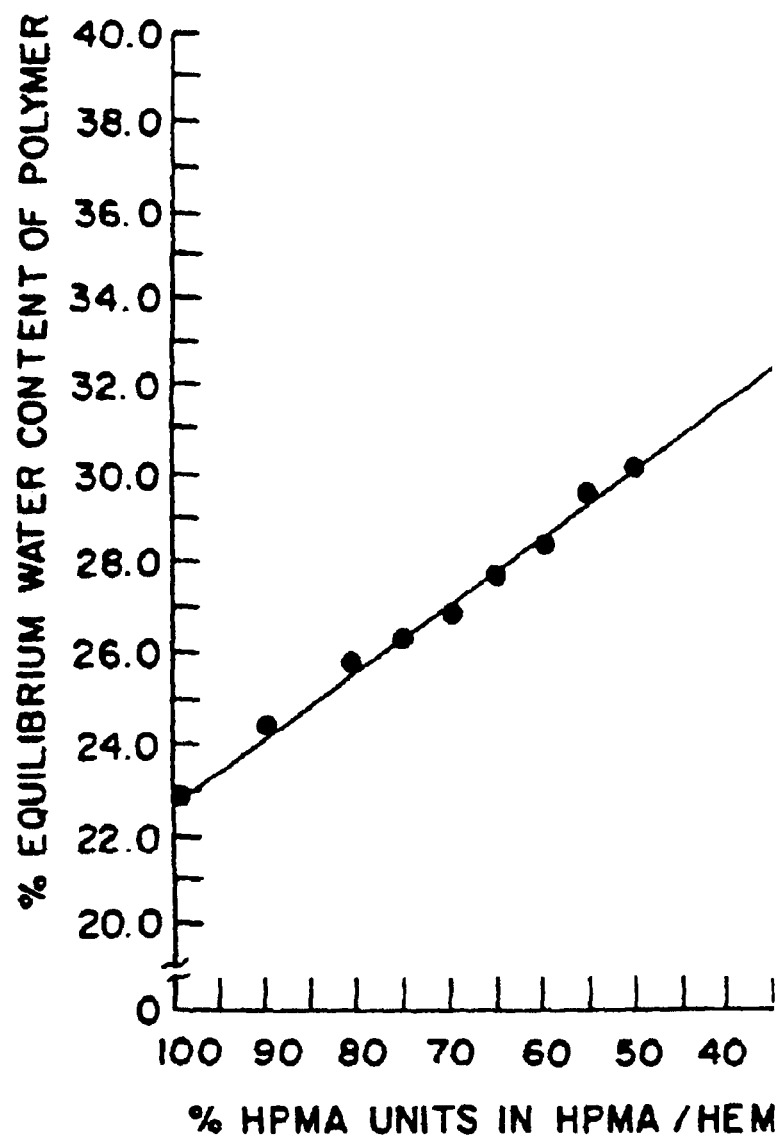
Figure 2:
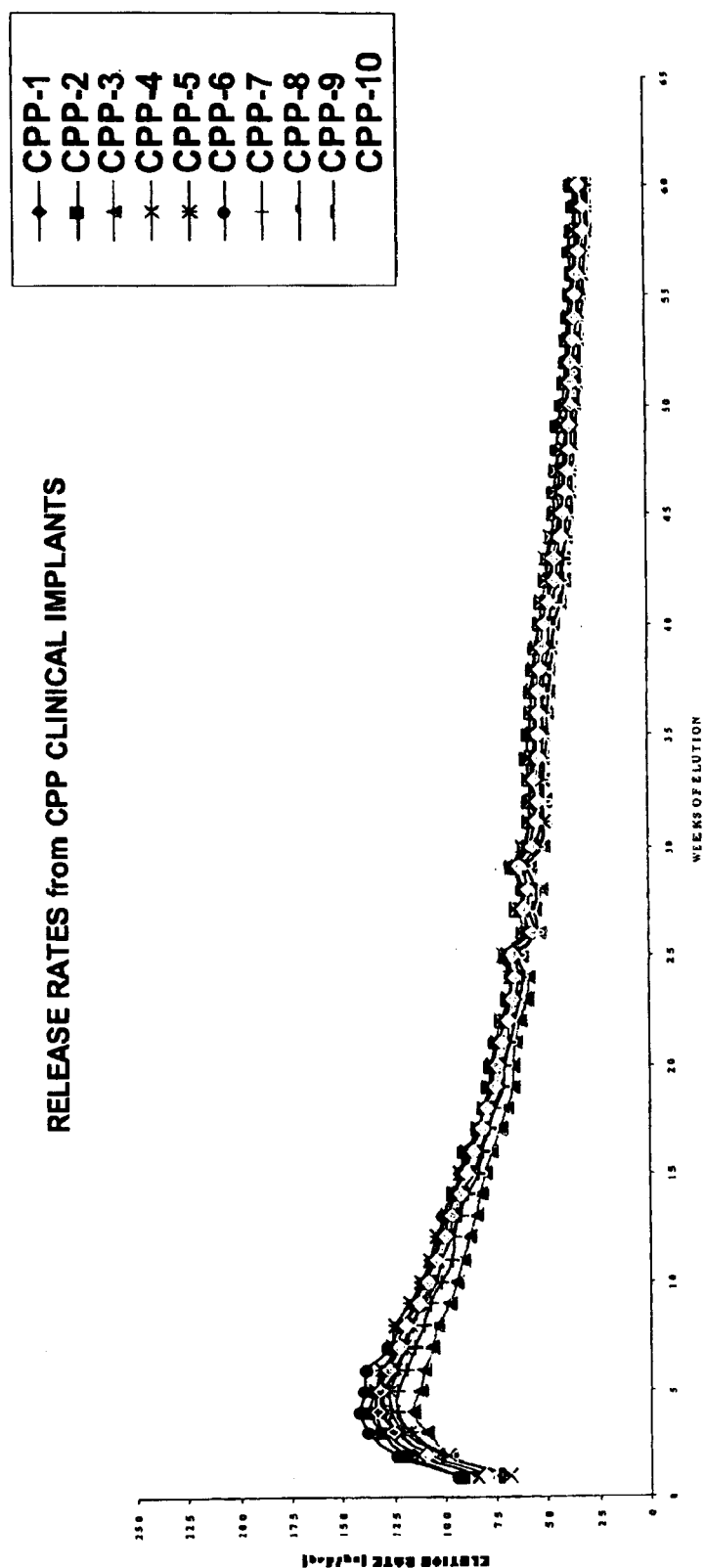
Figure 3A:
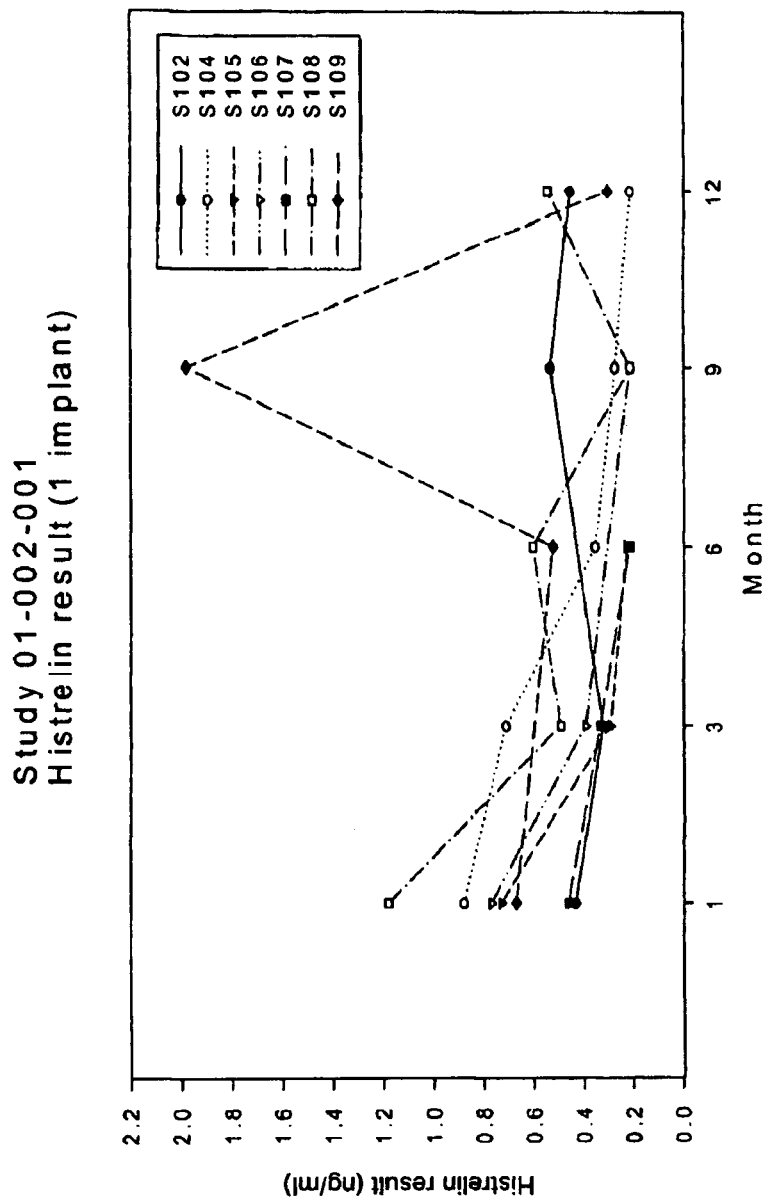
Figure 3B:
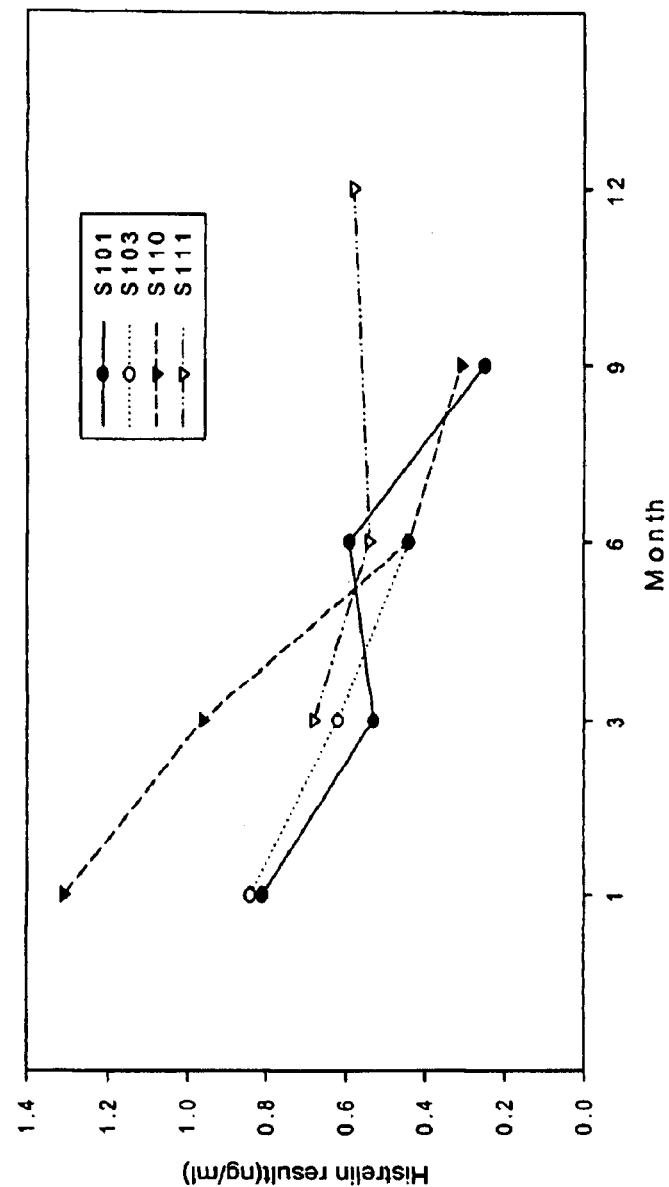
Figure 5:
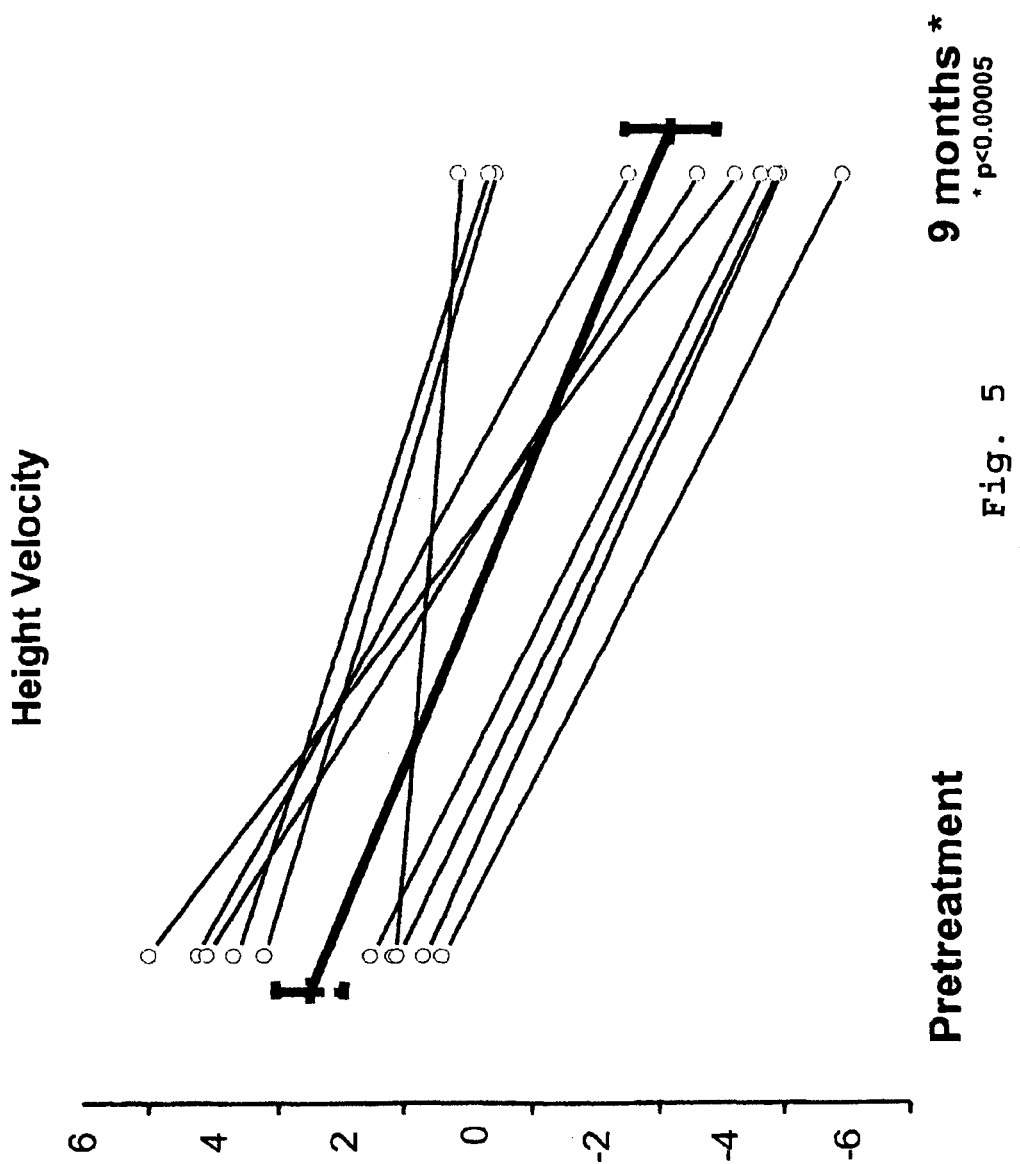
FIG. 5 is a graph of Height Velocity at pretreatment and 9 months following insertion of an histrelin implant of the present invention.
Figure 6:
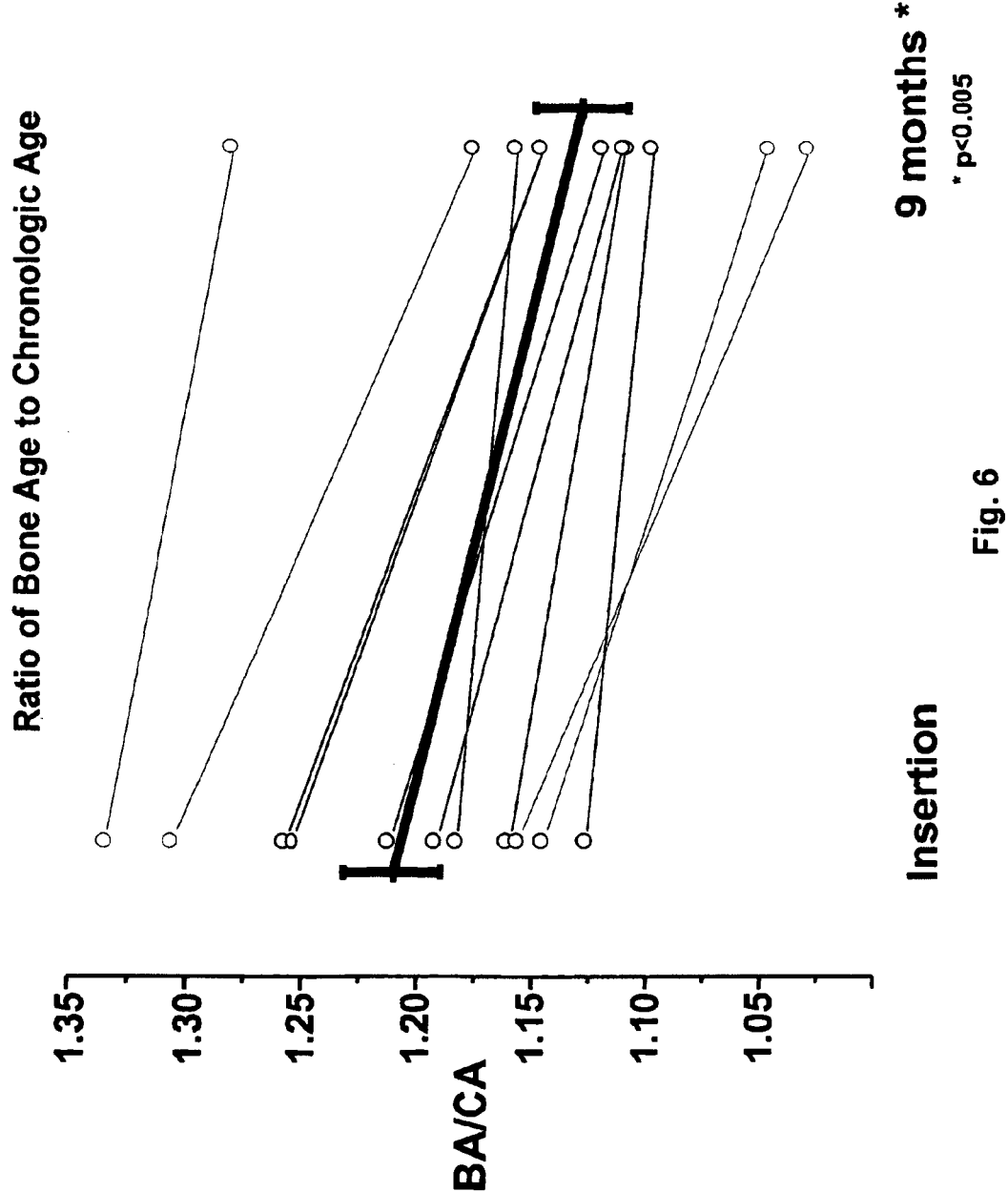

The height velocity at insertion and at nine months following implantation were measured. FIG. 5 illustrates the decrease of height velocity during treatment. Similarly, the bone age to chronologic age ratio was assessed at insertion and at nine months following implantation, as illustrated in FIG. 6.

Tanner Stage. The Tanner Stage is a subjective evaluation of sexual maturation. For the girls enrolled in this study, pubertal stages of breasts and pubic hair were rated on a scale of 1 to 5, where 5 represented the most advanced level of sexual maturation.

Figure 4:
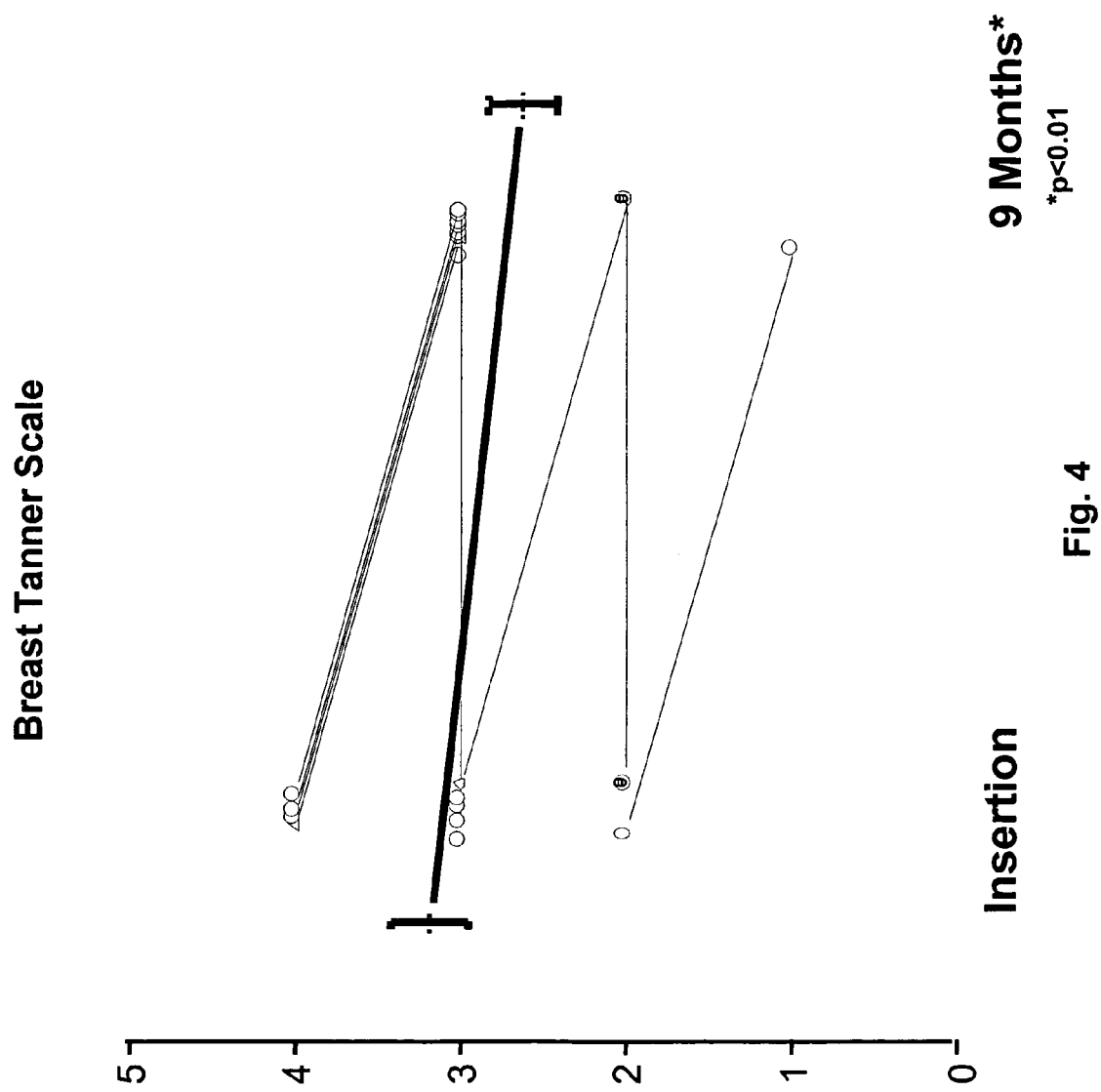
FIG. 4 is a graph of the Breast Tanner Scale at pretreatment and 9 months following insertion of an histrelin implant of the present invention.

Shift tables displaying changes in Tanner Stage from screening to each subsequent visit are presented in FIG. 4. At screening, two (18%) patients were rated Tanner Stage 2, five (45%) were rated Tanner Stage 3, and four (36%) were rated Tanner Stage 4 for breasts. All of the Stage 4 patients were rated Stage 3 at every evaluation from month 3 onward. One Stage 3 patient was rated Stage 2 at every evaluation from month 2 onward. Four Stage 3 patients were rated Stage 3 at all evaluations from month 2 to month 9. At month 12, three of those patients were rated Stage 3 whereas the fourth patient (Patient 101) was rated Stage 4. The latter patient was the only patient who had an increase in Tanner Stage for breast at any time during the study.

At screening, two (18%) patients were rated Tanner Stage 1, five (45%) were rated Stage 2, three (27%) were rated Stage 3, and one (9%) was rated Stage 4 for pubic hair. The only Stage 4 patient was rated Stage 3 at every evaluation from month 1 onward. Of the remaining patients, few had increases in Tanner Stage: one from Stage 1 to 2, two from Stage 2 to 3, and one from Stage 3 to 4.

Results and Conclusion. The results show that the histrelin implant maintains suppression of gonadotropins and estradiol for at least 12 months in girls with CPP. Skeletal maturation was significantly advanced at the time of implant insertion, but progressed more slowly during treatment.

There were no deaths or other serious adverse events during the first 12 montsh of treatment. One patient failed to complete 12 months of treatment because of an adverse event. Patient 103 was a 10-year-old girl who received two implants. She developed a local infection at the implant site, which resolved in 10 days after treatment with oral antibiotics. At Month 9, she was assigned to the first track and had her two original implants removed. A new implant was inserted in the same incision. A wound infection developed approximately 1 week after the new implant had been inserted. This infection also resolved after treatment with oral antibiotics. Ten days after insertion of the new implant, it was found to be partially extruded from the incision site and was removed. The patient withdrew from the study after the implant was removed. Seven (64%) patients experienced at least one adverse event during the study. The most commonly reported events were conditions related to the implant site and infections. All of the events were rated mild by the investigator.

What has been described and illustrated herein are embodiments of the invention along with some of their variations. The terms, descriptions and figures used herein are set forth by way of illustration only and are not meant as limitations. Those skilled in the art will recognize that many variations are possible within the spirit and scope of the invention, which is intended to be defined by the following claims and their equivalents in which all terms are meant in their broadest reasonable sense unless otherwise indicated.

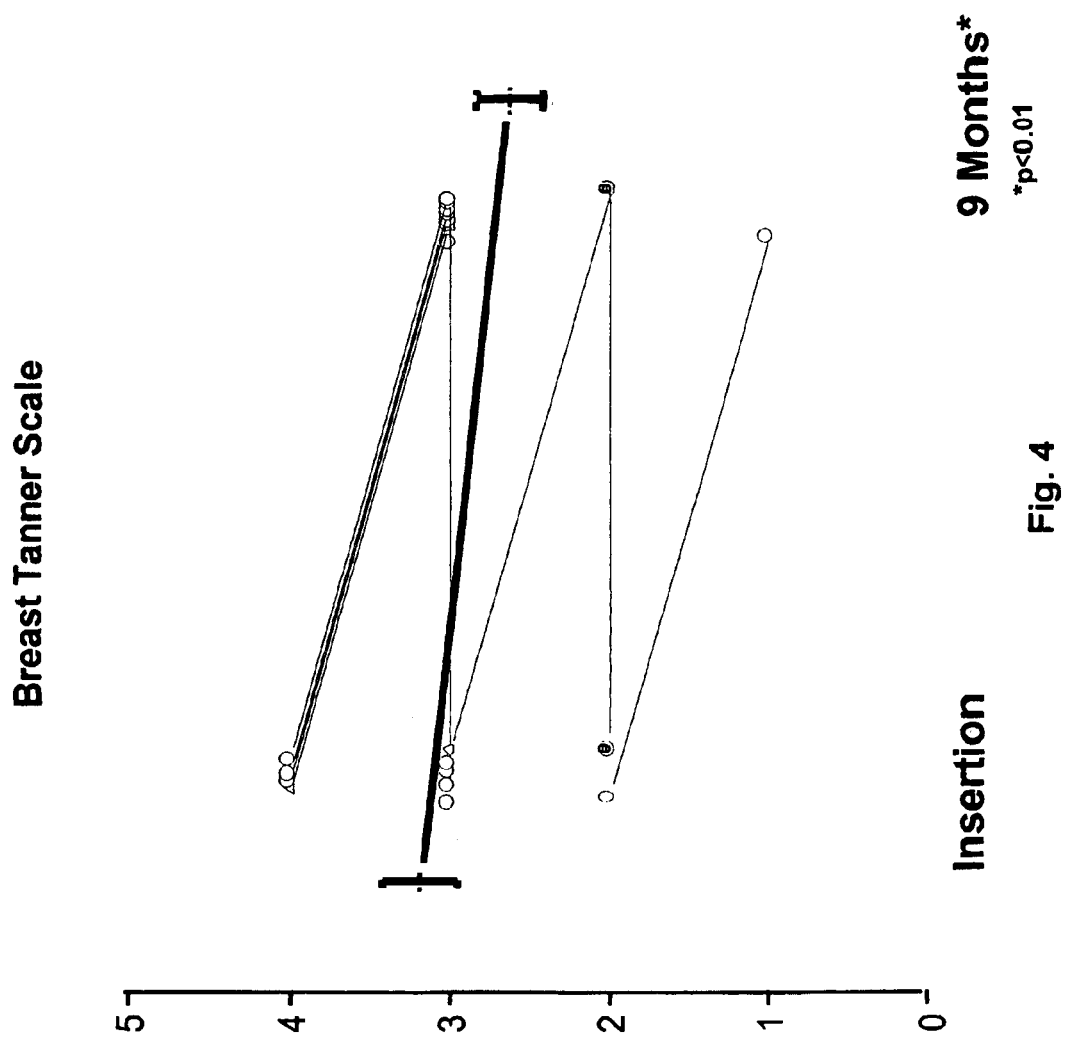

What is claimed is:

1. A method of treating central precocious puberty comprising:
   implanting subcutaneously into a patient in need thereof at least one controlled release reservoir implant containing a formulation comprising histrelin or its pharmaceutically acceptable salt, the reservoir implant comprising a hydrophilic copolymer obtained from a copolymerization of a mixture comprising at least two hydrophilic, ethylenically unsaturated monomers, and which implant provides an average in vivo release rate of about 60 μg to about 70 μg of the histrelin or its salt daily in the patient.

2. The method of claim 1, wherein said formulation comprises about 50 milligrams of histrelin or its salt.

3. The method of claim 1, wherein said histrelin is histrelin acetate.

4. The method of claim 1, wherein said implant releases a therapeutically effective amount of histrelin over about 2 months.

5. The method of claim 1, wherein said implant releases a therapeutically effective amount of histrelin over about 6 months.

6. The method of claim 1, wherein said implant releases a therapeutically effective amount of histrelin over about 12 months.

7. The method of claim 1, wherein said hydrophilic copolymer comprises 2-hydroxyethyl methacrylate and hydroxypropyl methacrylate.

8. The method of claim 7, wherein said hydrophilic copolymer further comprises a crosslinking agent.

9. The method of claim 8, wherein said crosslinking agent is trimethylolpropane trimethacrylate.

10. The method of claim 1, wherein said formulation further comprises stearic acid.

11. The method of claim 1, wherein said implant releases histrelin at a rate to maintain a mean plasma concentration of histrelin of about 0.2 ng/ml to about 2 ng/ml over at least two months.

12. The method of claim 1, wherein said implant releases histrelin at a rate to maintain a mean plasma concentration of histrelin of about 0.4 ng/ml to about 0.6 ng/ml over at least two months.

13. A method of treating central precocious puberty comprising:
    implanting subcutaneously into a patient in need thereof a controlled release reservoir implant containing a formulation comprising about 50 mg of histrelin acetate, the reservoir implant comprising a hydrophilic copolymer obtained from a copolymerization of a mixture comprising at least two hydrophilic, ethylenically unsaturated monomers, and which implant provides an average in vivo release rate of about 60 μg to about 70 μg of the histrelin acetate daily in the patient for 12 months.

14. A method of treating central precocious puberty comprising implanting subcutaneously into a patient in need thereof an implant comprising a hydrophilic copolymer and histrelin or its pharmaceutically acceptable salt, wherein said histrelin or its salt is contained within the hydrophilic copolymer, which is obtained from a copolymerization of a mixture comprising at least two hydrophilic, ethylenically unsaturated monomers, such that histrelin or its salt is released on average at a daily in vivo release rate of about 60 μg to about 70 μg to maintain a mean plasma concentration of histrelin of about 0.2 ng/ml to about 2 ng/ml over at least six months.

15. The method of claim 14, wherein histrelin is released at a rate to maintain a mean plasma concentration of histrelin of about 0.4 ng/ml to about 0.6 ng/ml over at least six months.

16. The method of claim 14 in which the histrelin comprises histrelin acetate.

17. The method of claim 15 further comprising removing the implant from the patient after about 12 months.

18. The method of claim 17 further comprising inserting a new implant into the patient.

* * * * *

UNITED STATES PATENT AND TRADEMARK OFFICE
CERTIFICATE OF CORRECTION

| | | |
|---|---|---|
| PATENT NO. | : 8,062,652 B2 | Page 1 of 1 |
| APPLICATION NO. | : 11/155822 | |
| DATED | : November 22, 2011 | |
| INVENTOR(S) | : Petr Kuzma | |

Figure 3:
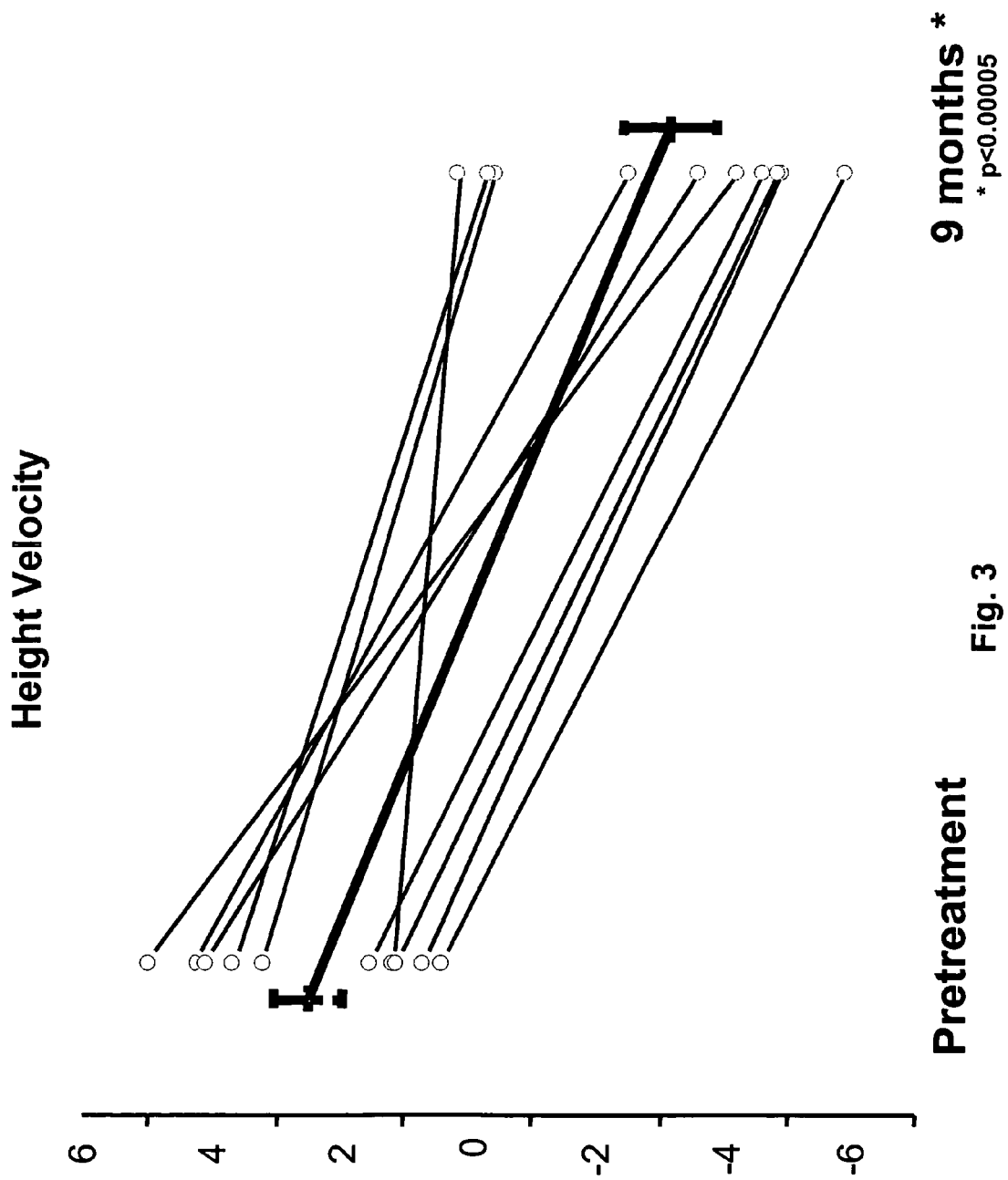
FIG. 3A is a graph of the serum histrelin concentrations for each patient with 1 implant (track 1) at all evaluation times and FIG. 3B is a graph of the serum histrelin concentrations for each patient with 2 implants (track 2) at all evaluation times.
Figure 3A:
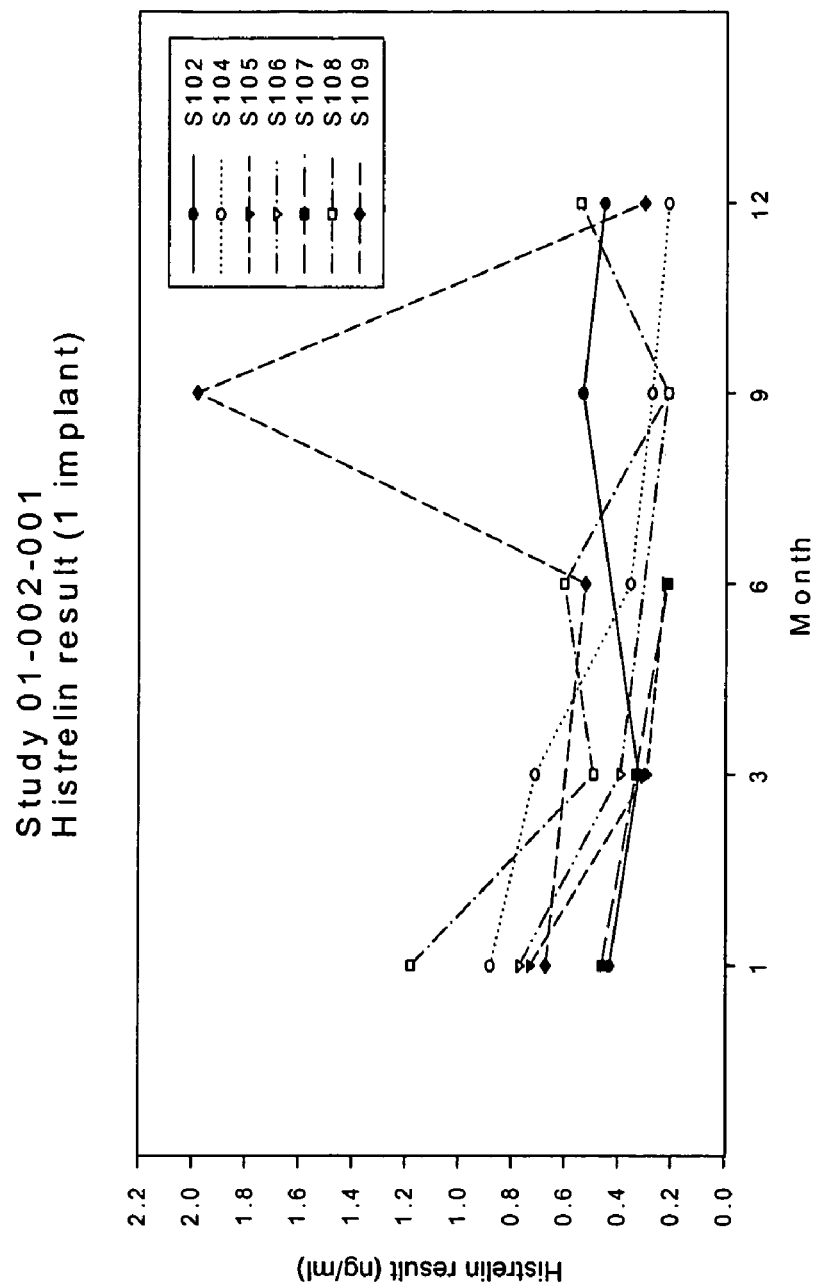
Figure 3B:
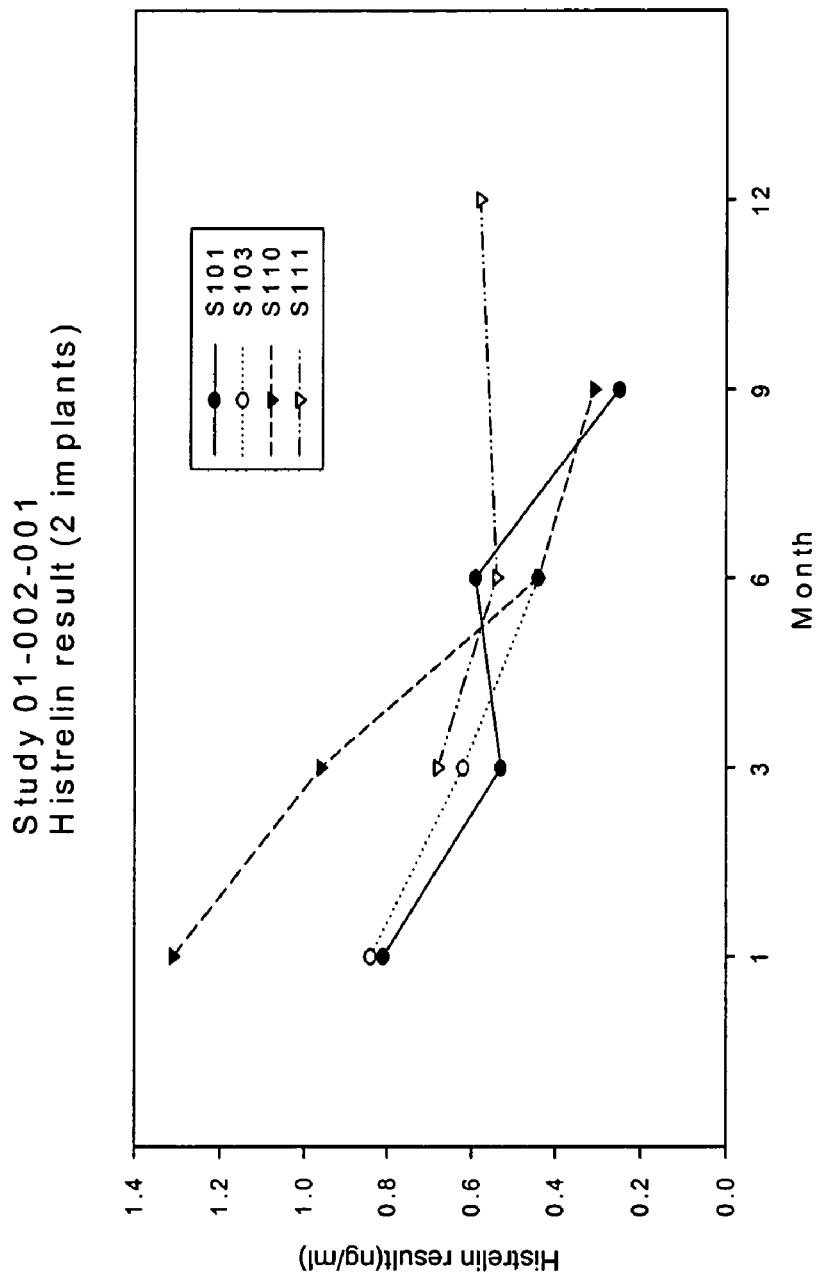

It is certified that error appears in the above-identified patent and that said Letters Patent is hereby corrected as shown below:

In the Drawings, Fig. 3 should be cancelled.

Signed and Sealed this
Fifteenth Day of May, 2012

David J. Kappos
*Director of the United States Patent and Trademark Office*

UNITED STATES PATENT AND TRADEMARK OFFICE
CERTIFICATE OF CORRECTION

PATENT NO. : 8,062,652 B2
APPLICATION NO. : 11/155822
DATED : November 22, 2011
INVENTOR(S) : Petr Kuzma et al.

Page 1 of 9

It is certified that error appears in the above-identified patent and that said Letters Patent is hereby corrected as shown below:

Delete the title page and substitute therefore the attached title page showing the corrected number of drawing sheets in patent.

Delete Drawing Sheets 1-8 and substitute therefore the attached Drawing Sheets 1-7.
FIG. 3 has been cancelled.

This certificate supersedes the Certificate of Correction issued May 15, 2012.

Signed and Sealed this
Twelfth Day of June, 2012

David J. Kappos
*Director of the United States Patent and Trademark Office*

(12) United States Patent
Kuzma

(10) Patent No.: US 8,062,652 B2
(45) Date of Patent: Nov. 22, 2011

(54) COMPOSITIONS AND METHODS FOR TREATING PRECOCIOUS PUBERTY

(75) Inventor: Petr Kuzma, Princeton, NJ (US)

(73) Assignee: Endo Pharmaceuticals Solutions Inc., Chadds Ford, PA (US)

( * ) Notice: Subject to any disclaimer, the term of this patent is extended or adjusted under 35 U.S.C. 154(b) by 364 days.

(21) Appl. No.: 11/155,822

(22) Filed: Jun. 17, 2005

(65) Prior Publication Data

US 2006/0019903 A1  Jan. 26, 2006

Related U.S. Application Data

(60) Provisional application No. 60/580,520, filed on Jun. 17, 2004.

(51) Int. Cl.
| | |
|---|---|
| *A61F 2/00* | (2006.01) |
| *A61K 38/00* | (2006.01) |
| *A61K 38/09* | (2006.01) |
| *A61K 31/765* | (2006.01) |
| *A61P 5/02* | (2006.01) |
| *A01N 31/14* | (2006.01) |

(52) U.S. Cl. ..... 424/423; 514/1.1; 514/10.3; 514/722.4; 514/899

(58) Field of Classification Search ........................ None
See application file for complete search history.

(56) References Cited

U.S. PATENT DOCUMENTS

| | | |
|---|---|---|
| 2,513,014 A | 6/1950 | Fields |
| 3,921,632 A | 11/1975 | Bardani |
| 4,285,987 A | 8/1981 | Ayer |
| 4,298,002 A | 11/1981 | Ronel et al. |
| 4,846,793 A | 7/1989 | Leonard et al. |
| 4,871,094 A | 10/1989 | Gall et al. |
| 4,959,217 A | 9/1990 | Sanders |
| 4,994,028 A | 2/1991 | Leonard et al. |
| 5,004,614 A | 4/1991 | Staniforth |
| 5,035,891 A | 7/1991 | Runkel et al. |
| 5,266,325 A | 11/1993 | Kuzma |
| 5,273,752 A | 12/1993 | Ayer |
| 5,292,515 A | 3/1994 | Moro |
| 5,614,223 A | 3/1997 | Sipos |
| 5,756,127 A | 5/1998 | Grisoni |
| 5,817,343 A | 10/1998 | Burke |
| 5,854,382 A | 12/1998 | Loomis |
| 5,876,761 A | 3/1999 | Bodmer et al. |
| 5,894,458 A * | 4/1999 | Takizawa et al. ............ 369/13.17 |
| 6,159,490 A | 12/2000 | Deghenghi |
| 6,337,318 B1 * | 1/2002 | Trigg et al. ..................... 514/15 |
| 6,361,797 B1 | 3/2002 | Kuzma et al. |
| 2004/0071736 A1 | 4/2004 | Quinn et al. |
| 2004/0097419 A1 | 5/2004 | Petersen et al. |
| 2005/0143303 A1 | 6/2005 | Quay et al. |

FOREIGN PATENT DOCUMENTS

| | | |
|---|---|---|
| EP | 0246653 | 11/1987 |
| EP | 314206 B1 | 5/1989 |
| EP | 0 384 646 A1 | 6/1993 |
| FR | 821383 A | 12/1937 |
| GB | 1 306 541 A | 2/1973 |
| WO | WO 98/44964 A1 | 10/1998 |
| WO | WO-02/49573 A2 | 6/2002 |
| WO | WO 02/078597 * | 10/2002 |
| WO | WO-2004/071736 A2 | 8/2004 |
| WO | WO 2005/013936 A2 | 2/2005 |
| WO | WO-2005/041873 A2 | 5/2005 |
| WO | WO-2006/099288 A2 | 9/2006 |
| WO | WO-2008/061355 A1 | 5/2008 |

OTHER PUBLICATIONS

Schlegel et al., Effective Long-Term Androgen Suppression in Men with Prostate Cancer using A Hydrogel Implant with the GnRH Agonist Histrelin, 2001, Urology 58(4):578-582.*
Langer, "Implantable Controlled Release Systems," Pharmac. Ther. (1983), vol. 21 pp. 35-51.*
Gennaro A.R., Remington: the Science and Practice of Pharmacy, 19th Edition, p. 1662.*
Lan NaLee, "Volume of Blood in a Human" from http://hypertextbook.com/facts/1998/LanNaLee.shtml, (1998) updated (2001.*
Shi et al. (Expert Opin. Drug Deliv. 2005, 2(6), pp. 1039-1058).*
Precocious Puberty [online] May 2010 retrieved from: http://www.childrensmemorial.org/depts/endocrinology/precocious-puberty.aspx; 4 pages.*
Ostrenski (Gynecology 2001, Lippinocott Williams & Wilkins, p. 12) 2 pages.*
Mayoclinic precocious puberty [online] retrieved from http://www.mayoclinic.com/health/precociouspuberty/DS00883 on Jul. 14, 2011; 9 pages.*
Burradell, L. B. et al., "Histrelin: A Review of its Pharmacological Properties and Therapeutic Role in Central Precocious Puberty," *Drugs*, vol. 45, No. 4, Apr. 1993, pp. 570-588; published by Adis International Limited.
Feuillan, P. P. et al., "Follow-up of children and young adults after GnRH-agonist therapy for central precocious puberty," *J. Endocrinol. Invest.*, vol. 24, 2001, pp. 734-736; published by Editrice Kurtis.
Berge, et al.,; "*Pharmaceutical Salts*" J. Pharm. Sci., 1977 66:1-19.
Higuchi, et al.; "*Pro-Drugs as Novel Delivery Systems*" vol. 14 of the ACS Symposium Series, 1975.
Roche, et al.,; "*Bioreversible Carriers in Drug Design*" American Pharm. Association and Pergamon Press, 1987.
Schlegel et al., Effective Long-Term Androgen Suppression in Men with Prostate Cancer using A Hydrogel Implant with the GnRH Agonist Histrelin, 2001, Urology 58(4):578-582.

(Continued)

*Primary Examiner* — Ernst Arnold
(74) *Attorney, Agent, or Firm* — Gilberto M. Villacorta; Jeffrey R. Lomprey; Foley & Lardner LLP

(57) ABSTRACT

The present invention is directed to the controlled delivery of gonadotropin-releasing hormone (GnRH) agonists, preferably from a polymeric material that is implanted in the body. More specifically, the present invention relates to compositions comprised of a GnRH agonist, preferably histrelin, in a polymeric material that results in a desired and controlled delivery of a therapeutically effective amount of GnRH agonist over an extended period of time in order to treat central precocious puberty (CPP).

18 Claims, 7 Drawing Sheets